US012611542B2

(12) United States Patent
Dinsmoor et al.

(10) Patent No.: US 12,611,542 B2
(45) Date of Patent: Apr. 28, 2026

(54) DIRECTIONAL ACTIVATION WITH ELECTRICAL STIMULATION

(71) Applicant: Medtronic, Inc., Minneapolis, MN (US)

(72) Inventors: David A. Dinsmoor, North Oaks, MN (US); Aleksandra P. Kharam, Maple Grove, MN (US); Leonid M. Litvak, Bet Shemesh (IL)

(73) Assignee: Medtronic, Inc., Minneapolis, MN (US)

( * ) Notice: Subject to any disclaimer, the term of this patent is extended or adjusted under 35 U.S.C. 154(b) by 354 days.

(21) Appl. No.: 18/322,034

(22) Filed: May 23, 2023

(65) Prior Publication Data

US 2023/0381521 A1 Nov. 30, 2023

Related U.S. Application Data

(60) Provisional application No. 63/365,565, filed on May 31, 2022.

(51) Int. Cl.
*A61N 1/36* (2006.01)

(52) U.S. Cl.
CPC ..... *A61N 1/36139* (2013.01); *A61N 1/36062* (2017.08)

(58) Field of Classification Search
None
See application file for complete search history.

(56) References Cited

U.S. PATENT DOCUMENTS

| | | | |
|---|---|---|---|
| 7,634,315 | B2 | 12/2009 | Cholette |
| 9,155,892 | B2 | 10/2015 | Parker et al. |
| 2019/0298992 | A1 | 10/2019 | Zhang et al. |
| 2020/0147390 | A1 | 5/2020 | Zhang et al. |
| 2021/0121700 | A1* | 4/2021 | Dinsmoor .......... A61N 1/36139 |
| 2021/0187300 | A1 | 6/2021 | Dinsmoor et al. |

(Continued)

FOREIGN PATENT DOCUMENTS

| | | |
|---|---|---|
| WO | 2021119741 A1 | 6/2021 |
| WO | 2021146774 A1 | 7/2021 |

OTHER PUBLICATIONS

Extended Search Report from counterpart European Application No. 23176334.3 dated Oct. 23, 2023, 8 pp.

(Continued)

*Primary Examiner* — Carl H Layno
*Assistant Examiner* — Bryan McAllister Lee
(74) *Attorney, Agent, or Firm* — Shumaker & Sieffert, P.A.

(57) ABSTRACT

For example, a system includes stimulation generation circuitry configured to deliver a multiphasic stimulation pulse to the patient and sensing circuitry configured to sense a composite evoked compound action potential (ECAP) signal elicited by the multiphasic stimulation pulse. The system further includes processing circuitry electrically connected to the sensing circuitry and the stimulation generation circuitry, the processing circuitry being configured to control the stimulation generation circuitry to deliver the multiphasic stimulation pulse that comprises a first phase and a second phase and determine, based on the composite ECAP signal, a propagation characteristic for the composite ECAP signal that is elicited by the multiphasic stimulation pulse.

29 Claims, 12 Drawing Sheets

(56)             References Cited

U.S. PATENT DOCUMENTS

| | | |
|---|---|---|
| 2021/0252289 A1 | 8/2021 | Esteller |
| 2022/0007987 A1* | 1/2022 | Huang ................. A61B 5/4041 |
| 2022/0062639 A1 | 3/2022 | Dinsmoor et al. |

OTHER PUBLICATIONS

Response to Extended Search Report dated Oct. 23, 2023, from counterpart European Application No. 23176334.3 filed Jun. 3, 2024, 17 pp.

Communication pursuant to Article 94(3) EPC from counterpart European Application No. 23176334.3 dated May 28, 2025, 6 pp.

* cited by examiner

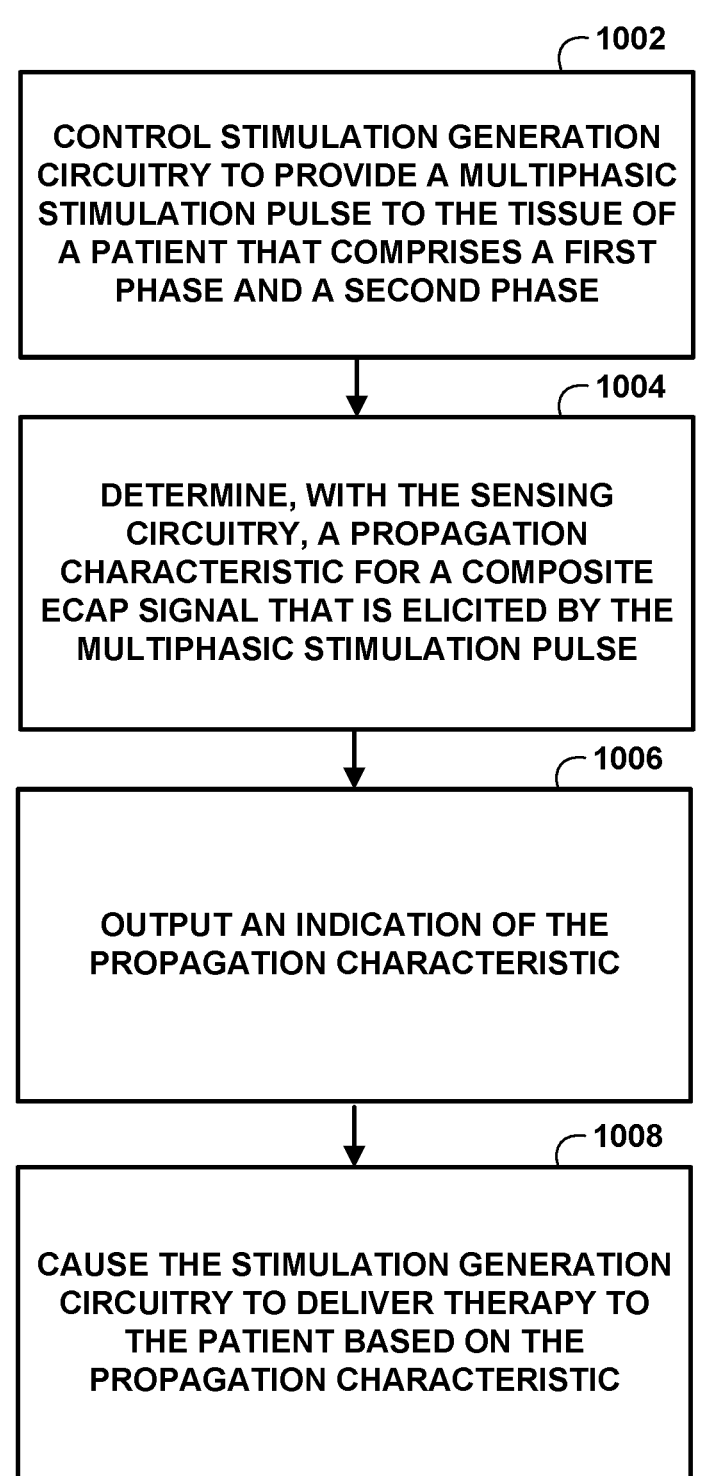

1002

CONTROL STIMULATION GENERATION CIRCUITRY TO PROVIDE A MULTIPHASIC STIMULATION PULSE TO THE TISSUE OF A PATIENT THAT COMPRISES A FIRST PHASE AND A SECOND PHASE

1004

DETERMINE, WITH THE SENSING CIRCUITRY, A PROPAGATION CHARACTERISTIC FOR A COMPOSITE ECAP SIGNAL THAT IS ELICITED BY THE MULTIPHASIC STIMULATION PULSE

1006

OUTPUT AN INDICATION OF THE PROPAGATION CHARACTERISTIC

1008

CAUSE THE STIMULATION GENERATION CIRCUITRY TO DELIVER THERAPY TO THE PATIENT BASED ON THE PROPAGATION CHARACTERISTIC

FIG. 10

DIRECTIONAL ACTIVATION WITH ELECTRICAL STIMULATION

This application claims the benefit of U.S. Provisional Patent Application No. 63/365,565, filed 31 May 2022, the entire contents of which is incorporated herein by reference.

TECHNICAL FIELD

This disclosure generally relates to electrical stimulation, and more specifically, control of electrical stimulation.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation can result in an evoked compound action potential (ECAP) from nerves within the patient.

SUMMARY

In general, systems, devices, and techniques are described herein for determining a propagation characteristic for an evoked action potential (ECAP) signal resulting from a stimulation pulse. The propagation characteristic may be utilized as a feedback variable to select or adjust electrical stimulation therapy delivered to a patient. An ECAP signal may refer to a measure of the nerve tissue's response to stimulation. For example, in response to a cathodic phase of a multiphasic stimulation pulse, a set of nerves may depolarize which can result in a first ECAP signal detectable by sensing circuitry. In response to an anodic phase of the stimulation pulse, the same set, or a different set, of nerves may depolarize which can result in a second ECAP signal detectable by sensing circuitry. The first ECAP signal and the second ECAP signal may result in a set of ECAP signals that may be detected by sensing circuitry. The characteristics of the set of ECAP signals, which may also be referred to herein as simply a "composite ECAP signal" may include, for example, an amplitude value, which may be a function of the number of nerves or nerve fibers that depolarized in response to the stimulation as well as a propagation characteristic of the composite ECAP signal. Further, the amplitude value of the composite ECAP signal may also be a function of a propagation characteristic of the composite ECAP signal, such as, for example, a time delay between the first ECAP signal and the second ECAP signal. The time delay between the first ECAP signal and the second ECAP signal may result in a destructive interference (e.g., lower amplitude due to the propagation parameter) or constructive interference (e.g., a higher amplitude due to the propagation parameter). Medical devices can provide more effective therapy by adjusting, based on the propagation characteristic, one or more parameters that define stimulation.

For example, a medical device may adjust a pulse width, interval between the cathodic phase and the anodic phase, and/or select electrodes with a desirable spatial distance to apply destructive interference to reduce an ECAP amplitude and/or apply constructive interference to increase an ECAP amplitude. Reducing the ECAP amplitude using destructive interference may help to improve treatment, for example, by reducing the ECAP signal in the rostral direction towards the brain, which may reduce negative side effects, or changing the relative timing of the two trains such that one of the two signals effectively masks the other signal, and thereby less excitation is achieved in the central structures. In some examples, increasing the ECAP amplitude in the rostral direction towards the distal end of the spinal cord using constructive interference may help to improve treatment, for example, by decreasing an amount of electrical stimulation provided to nerves, which may reduce the affects of paresthesia and/or reduce an amount of energy used to provide the electrical stimulation.

In one example, a system includes stimulation generation circuitry configured to deliver a multiphasic stimulation pulse to the patient and sensing circuitry configured to sense a composite ECAP signal elicited by the multiphasic stimulation pulse. The system further includes processing circuitry electrically connected to the sensing circuitry and the stimulation generation circuitry, the processing circuitry being configured to control the stimulation generation circuitry to deliver the multiphasic stimulation pulse that comprises a first phase and a second phase and determine, based on the composite ECAP signal, a propagation characteristic for the composite ECAP signal that is elicited by the multiphasic stimulation pulse.

In another example, a method includes controlling stimulation generation circuitry to deliver a multiphasic stimulation pulse that comprises a first phase and a second phase and determining, based on a composite ECAP signal elicited by the multiphasic stimulation pulse, a propagation characteristic for the composite ECAP signal.

In one example, a medical device includes stimulation generation circuitry configured to deliver a multiphasic stimulation pulse to the patient and sensing circuitry configured to sense ECAP signals elicited by the multiphasic stimulation pulse. The medical device further includes processing circuitry electrically connected to the sensing circuitry and the stimulation generation circuitry, the processing circuitry being configured to control the stimulation generation circuitry to deliver the multiphasic stimulation pulse that comprises a first phase and a second phase and determine, based on the ECAP signals, a propagation characteristic for a set of the ECAP signals that are elicited by the multiphasic stimulation pulse.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages of the techniques will be apparent from the description and drawings, and from the claims.

BRIEF DESCRIPTION OF DRAWINGS

FIG. 10 is a flowchart illustrating an example operation for providing therapy, in accordance with one or more techniques of this disclosure.

DETAILED DESCRIPTION

Figure 1:
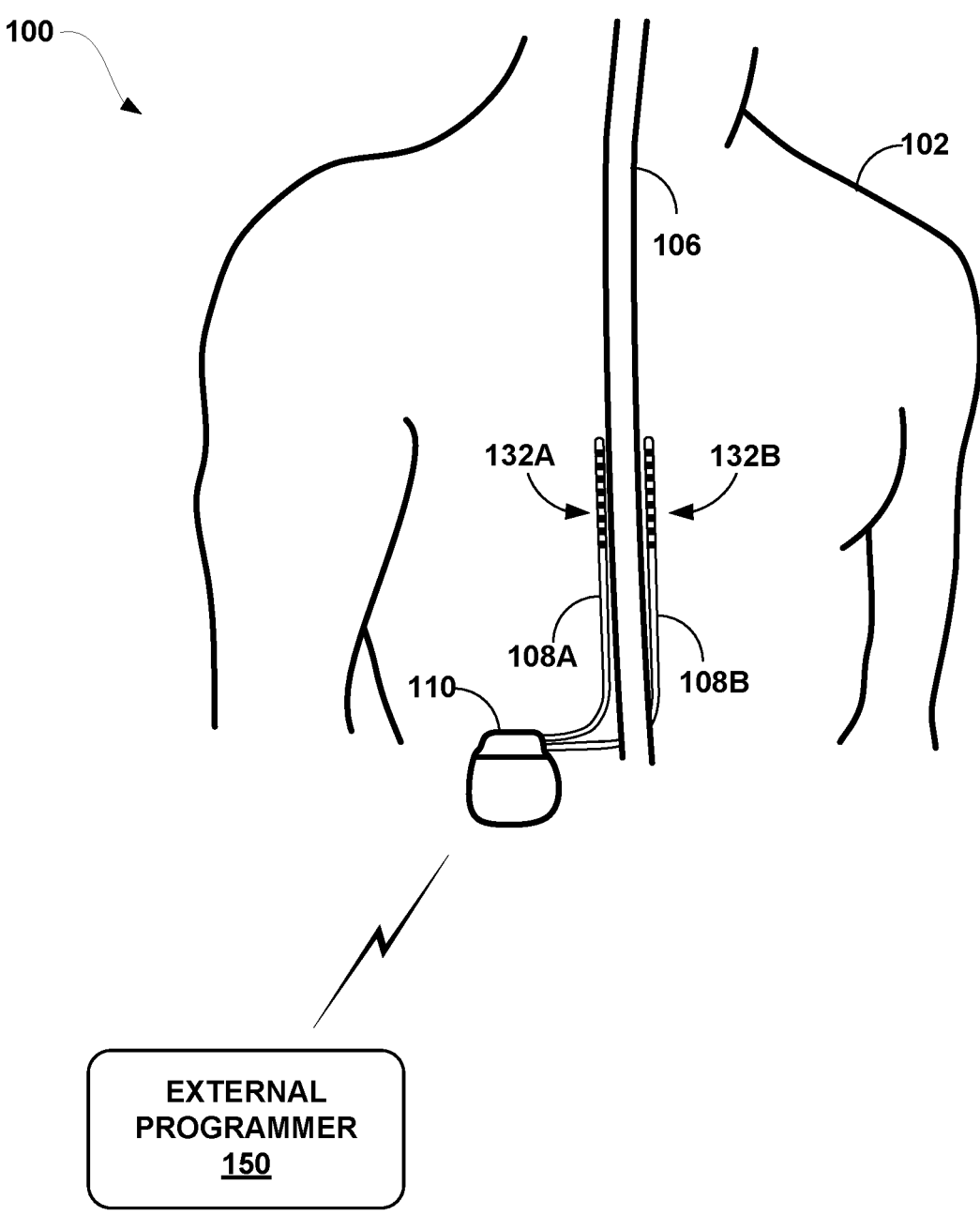
FIG. 1 is a conceptual diagram illustrating an example system that includes an implantable medical device (IMD) according to the techniques of the disclosure.

The disclosure describes examples of medical devices, systems, and techniques for determining a propagation characteristic for an evoked action potential (ECAP) signal resulting from a stimulation pulse to help to provide electrical stimulation therapy to a patient. Electrical stimulation therapy can be delivered to a target tissue (e.g., nerves of the spinal cord or muscle) of a patient via two or more electrodes. The two or more electrodes may deliver control pulses configured to elicit an ECAP signal from nerve tissue of a patient, or deliver informed pulses configured to deliver therapy to the patient. In this disclosure, "control pulses" may be stimulation pulses that are configured to elicit detectable ECAP signals. The control pulses may provide therapeutic effect, but need not necessarily provide therapeutic effect. "Informed pulses" may be stimulation pulses that are configured to contribute to a therapeutic effect. ECAP signals may or may not be elicited by informed pulses. Informed pulses may be "informed" in the sense that the parameters of the informed pulses (e.g., an amplitude, a pulse width, or a frequency) may be based on sensed ECAP signals that were elicited by the control pulses. The informed pulses may be considered as providing governing therapy or governed therapy. Governing therapy or governed therapy may indicate that the stimulation pulses are for effective therapy.

Parameters of the electrical stimulation therapy (e.g., an electrode combination, a voltage amplitude, a current amplitude, a pulse width, or a pulse frequency) may be selected by a clinician and/or the patient to provide relief from various symptoms, such as pain, nervous system disorders, muscle disorders, etc. In accordance with the techniques of the disclosure, parameters of the electrical stimulation therapy (e.g., informed pulses) may be adjusted in response to a propagation characteristic of the ECAP signal. In some examples, a medical device may apply constructive interference and/or destructive interference for the signals elicited by each phase of the biphasic pulse using the propagation characteristic of the ECAP signal.

For example, a medical device may adjust a pulse width, interval between a cathodic phase of biphasic stimulation and the anodic phase of the biphasic stimulation (e.g., biphasic stimulation being one example of multiphasic stimulation), and/or select electrodes with a desirable spatial distance that results in destructive interference between the ECAP signals from respective phases of the biphasic pulse to reduce an overall ECAP amplitude of a composite ECAP and/or result in constructive interference between the ECAP signals from respective phases of the biphasic pulse to reduce an overall ECAP amplitude of the composite ECAP. Reducing the ECAP amplitude using destructive interference may help to improve therapy efficacy, for example, by reducing the ECAP signal amplitude in the rostral direction towards the brain, which may reduce undesirable side effects, such as tingling or stimulation perception. In some examples, increasing the ECAP amplitude in the caudal direction towards the distal end of the spinal cord using constructive interference may help to improve therapy efficacy, for example, by decreasing an amount of electrical stimulation needed to reduce the perception of pain, which may reduce the effects of paresthesia and/or reduce an amount of energy needed to provide efficacious therapy via electrical stimulation.

FIG. 1 is a conceptual diagram illustrating an example system 100 that includes an IMD 110 according to the techniques of the disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

In accordance with the techniques of the disclosure, IMD 110 may be configured to determine a propagation characteristic for a set of ECAP signals that are elicited by a stimulation pulse. For example, IMD 110 may determine a time delay between a first ECAP signal that is responsive to a cathodic phase of a multiphasic stimulation pulse and a second ECAP signal that is responsive to a anodic phase of the multiphasic stimulation pulse. In this way, system 100, patient 102, or a clinician may more quickly and more accurately configure program parameters (e.g., a pulse width, an interval between the cathodic phase and the anodic phase, or select electrodes) based on the determined propagation characteristic (e.g., the time delay). While this example describes the propagation characteristic as a time delay, the propagation characteristic may additionally or alternatively include other information, such as, for example, a conduction velocity or a launch time as described further below. Moreover, in some examples, IMD 110 or another device of system 100 may determine the program parameters without user input. IMD 110 may then apply the determined program parameters with or without user input (e.g., a confirmation input).

As shown in FIG. 1, system 100 includes an IMD 110, leads 108A and 108B, and external programmer 150 shown in conjunction with a patient 102, who is a human patient. In the example of FIG. 1, IMD 110 is an implantable electrical stimulator that is configured to generate and deliver electrical stimulation therapy to patient 102 via one or more electrodes of electrodes 132A and/or 132B (collectively, "electrodes 132") of leads 108A and/or 108B (collectively, "leads 108"), e.g., for relief of chronic pain or other symptoms. In other examples, IMD 110 may be coupled to a single lead carrying multiple electrodes or more than two leads each carrying multiple electrodes. In some examples, the stimulation signals, or pulses (e.g., control pulses), may be configured to elicit detectable ECAP signals that IMD 110 may use to determine the posture state occupied by patient 102 and/or determine how to adjust one or more parameters that define stimulation therapy. The control pulses may provide therapeutic effect, but in one or more examples, the control pulses may not provide therapeutic effect. IMD 110 may be configured to delivered informed pulses for providing therapeutic effect. The informed pulses may be "informed" because the parameters of the informed pulses may be based on the ECAP signal generated from the delivery of control pulses. The informed pulses may be considered as providing governed therapy. Governing therapy may indicate that the stimulation pulses are for effective therapy. The control pulses may be "control" because the delivery of the control pulses is used to control the parameters for the informed pulses.

IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102. In some examples, a medical device, configured to perform techniques similar to IMD 110, may be an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes 132 of implantable leads 108. In the example of FIG. 1, leads 108 carry electrodes 132 that are placed adjacent to the target tissue of spinal cord 106. One or more of electrodes 132 may be disposed at a distal tip of a lead 108 and/or at other positions at intermediate points along the lead. Leads 108 may be implanted and coupled to IMD 110. Electrodes 132 may transfer electrical stimulation generated by an electrical stimulation generator in IMD 110 to tissue of patient 102. Although leads 108 may each be a single lead, lead 108 may include a lead extension or other segments that may aid in implantation or positioning of lead 108. In some examples, IMD 110 may be a leadless stimulator with one or more arrays of electrodes arranged on a housing of the stimulator rather than leads that extend from the housing. In addition, in some examples, system 100 may include one lead or more than two leads, each coupled to IMD 110 and directed to similar or different target tissue sites.

Electrodes 132 of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 108 will be described for purposes of illustration.

The deployment of electrodes 132 via leads 108 is described for purposes of illustration, but arrays of electrodes 132 may be deployed in different ways. For example, a housing associated with a leadless stimulator may carry arrays of electrodes 132, e.g., rows and/or columns (or other patterns), to which shifting operations may be applied. Such electrodes 132 may be arranged as surface electrodes, ring electrodes, or protrusions. As a further alternative, electrode arrays may be formed by rows and/or columns of electrodes 132 on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 108 are linear leads having 8 ring electrodes along the axial length of the lead. In another example, electrodes 132 are segmented rings arranged in a linear fashion along the axial length of the lead and at the periphery of the lead.

The stimulation parameter set of a stimulation program that defines the stimulation pulses of electrical stimulation therapy by IMD 110 through the electrodes of leads 108 may include information identifying which electrodes 132 have been selected for delivery of stimulation according to a stimulation program, the polarities of the selected electrodes 132, e.g., an electrode combination for the program, a voltage amplitude, a current amplitude, a pulse frequency, a pulse width, or a pulse shape of stimulation delivered by electrodes 132. These stimulation parameters values that make up the stimulation parameter set that defines pulses may be predetermined parameter values defined by a user and/or automatically determined by system 100 based on one or more factors or user input. Informed pulses may be defined by a set of informed stimulation parameter values and control pulses may be defined by a set of control stimulation parameter values.

Although FIG. 1 is directed to SCS therapy, e.g., used to treat pain, in other examples system 100 may be configured to treat any other condition that may benefit from electrical stimulation therapy. In some examples, system 100 may be configured to provide multimodal stimulation using prime stimulation and base stimulation together. In some examples, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of spinal cord stimulation (SCS), deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, lead 108 includes one or more sensors configured to allow IMD 110 to monitor one or more parameters of patient 102, such as patient activity, pressure, temperature, or other characteristics. The one or more sensors may be provided in addition to, or in place of, therapy delivery by lead 108. Rather than or in addition to lead 108 including such sensors, IMD 110 may include such sensors.

IMD 110 may be configured to deliver electrical stimulation therapy (e.g., informed pulses and/or control pulses in the form of a prime pulse train and base pulse train, respectively) to patient 102 via selected combinations of electrodes 132 carried by one or both of leads 108, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 106, such as within an intrathecal space or epidural space of spinal cord 106, or, in some examples, adjacent nerves that branch off spinal cord 106.

Leads 108 may be introduced into spinal cord 106 in via any suitable region, such as the thoracic, cervical, or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results. In some examples, stimulation of spinal cord 106 or other anatomical structures associated with the spinal cord (e.g., nerves and cells associated with the nervous system) may provide relief from symptoms that may not produce paresthesia. For example, IMD 110 may deliver stimulation with intensities (e.g., amplitude values and/or pulse width values) below a sensory or perception threshold (e.g., sub-threshold stimulation) that reduces pain without paresthesia. In multimodal stimulation, for example, IMD 110 may deliver one pulse train at a higher frequency via one electrode combination and a second pulse train on an interleaved basis with a lower frequency via a second electrode combination, where both pulse trains are delivered at a sub-threshold intensity.

IMD 110 may be configured to generate and deliver electrical stimulation therapy to a target stimulation site within patient 102 via electrodes 132 of leads 108 to patient 102 according to one or more therapy stimulation programs.

A therapy stimulation program may generally define informed pulses, but may also define control pulses if the control pulses also contribute to a therapeutic effect. A therapy stimulation program may define values for one or more parameters (e.g., a parameter set) that define an aspect of the therapy delivered by IMD 110 according to that program. For example, a therapy stimulation program that controls delivery of stimulation by IMD 110 in the form of pulses may define a voltage, a current, a pulse width, a pulse rate (e.g., a pulse frequency), an electrode combination, or a pulse shape for stimulation pulses delivered by IMD 110 according to that program. In some examples, one or more therapy stimulation programs define multiple different pulse trains that have different parameter values (e.g., different pulse frequencies, amplitude values, pulse widths, and/or electrode combinations) but are delivered on an interleaved basis to together provide a therapy for patient 102.

As discussed further herein, IMD 110 may determine a propagation parameter of an ECAP signal and output indication of the propagation parameter and/or apply therapy using the propagation parameter. For example, patient 102 or a caretaker of patient 102 may select one or more of a voltage, a current, a pulse width, a pulse rate (e.g., a pulse frequency), an electrode combination, or a pulse shape for stimulation pulses delivered by IMD 110 based on the propagation parameter. In some examples, IMD 110 may select one or more of a voltage, a current, a pulse width, a pulse rate (e.g., a pulse frequency), an electrode combination, or a pulse shape for stimulation pulses delivered by IMD 110 based on the propagation parameter, e.g., without user input. IMD 110 may determine the propagation parameter for each positional state (e.g., prone, supine, etc.).

IMD 110 may determine the propagation parameter periodically (e.g., daily, monthly, weekly, etc) and/or based on an event (e.g., a diagnostic of IMD 110, a clinician visit, etc.). While examples described herein refer to a single propagation parameter, IMD 110 may determine multiple propagation characteristics, for example, a first time delay between the cathodic phase and the anodic phase in the caudal direction of the distal end of the spinal cord of patient 102 and a second time delay between the cathodic phase and the anodic phase in the rostral direction toward the brain of patient 102. Moreover, IMD 110 may determine multiple propagation characteristics for one direction. For example, IMD 110 may determine a first conduction velocity for the cathodic phase in the direction of the brain and a second conduction velocity for the anodic phase in the direction of the brain.

Furthermore, IMD 110 may be configured to deliver control stimulation to patient 102 via a combination of electrodes 132 of leads 108, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes of electrodes 132. Because control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode 132 combination for informed pulses (i.e., governed therapy). Like the electrical stimulation therapy, the control stimulation may be in the form of electrical stimulation pulses or continuous waveforms.

For example, each control stimulation pulse may include a multiphasic pulse, such as a balanced, biphasic square pulse that employs an active recharge phase. A multiphasic pulse may include two or more phases, where each phase is a duration of current delivered at one polarity (e.g., cathodic or anodic). Another example of a multiphasic pulse is a three phase pulse with either two anodic phases and one anodic phase or two anodic phases and one cathodic phase. However, in other examples, the control stimulation pulses may include a monophasic pulse followed by a passive recharge phase. In other examples, a control pulse may include an imbalanced biphasic portion and a passive recharge portion. Although not necessary, a multiphasic control pulse (e.g., a biphasic pulse) may include an interphase interval between the positive and negative phase(s) to promote propagation of the nerve impulse in response to the first phase of the multiphasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes 132 on leads 108. In cases where the control stimulation pulses are applied to spinal cord 106, the signal may be sensed by IMD 110 from spinal cord 106.

A user, such as a clinician or patient 102, may interact with a user interface of an external programmer 150 to program IMD 110. Programming of IMD 110 may refer generally to the generation and transfer of commands, programs, or other information to control the operation of IMD 110. In this way, IMD 110 may receive the transferred commands and programs from external programmer 150 to control stimulation, such as stimulation pulses that provide electrical stimulation therapy. For example, external programmer 150 may transmit therapy stimulation programs, stimulation parameter adjustments, therapy stimulation program selections, posture states, user input, or other information to control the operation of IMD 110, e.g., by wireless telemetry or wired connection.

In some examples, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this way, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, may deliver electrical stimulation therapy (e.g., informed pulses and/or control pulses) according to a plurality of therapy stimulation programs to a target tissue site of the spinal cord 106 of patient 102 via electrodes 132 on leads 108. In some examples, IMD 110 may modify therapy stimulation programs as therapy needs of patient 102 evolve over time. For example, the modification of the therapy stimulation programs may cause the adjustment of at least one parameter of the plurality of stimulation pulses. When patient 102 receives the same therapy for an extended period, the efficacy of the therapy may be reduced. In some cases, parameters of the plurality of stimulation pulses may be automatically (e.g., without user input) updated, for example, by IMD 110, external programmer 150 or another device or cloud system.

Efficacy of electrical stimulation therapy may be indicated by one or more features (e.g., an amplitude value between one or more peaks or an area under the curve of one or more peaks) of an action potential that is evoked by a control pulse delivered by IMD 110 (e.g., a characteristic value of the ECAP signal). Electrical stimulation therapy delivery by leads 108 of IMD 110 may cause neurons within the target tissue to evoke a compound action potential that travels up and down the target tissue, eventually arriving at sensing electrodes of IMD 110 (e.g., electrodes of electrodes 132 that are assigned for sensing). For instance, stimulation may elicit at least one ECAP signal, and ECAP responsive to stimulation may also be a surrogate for the effectiveness of the therapy. The amount of action potential (e.g., number of neurons propagating action potential signals) that are evoked may be based on the various parameters of electrical stimulation pulses such as an amplitude value, a pulse width, a frequency, a pulse shape (e.g., slew rate at the beginning and/or end of the pulse), or a propagation parameter. The slew rate may define the rate of change of the voltage amplitude value and/or current amplitude value of the control pulse at the beginning and/or end of each control pulse or each phase within the pulse. For example, a very high slew rate indicates a steep or even near vertical edge of the pulse, and a low slew rate indicates a longer ramp up (or ramp down) in the amplitude value of the control pulse. In some examples, these parameters contribute to an intensity of the electrical stimulation. In addition, a characteristic of the ECAP signal (e.g., an amplitude value) may change based on the distance between the stimulation electrodes and the nerves subject to the electrical field produced by the delivered control pulses.

Some example techniques for adjusting stimulation parameter values for stimulation pulses (e.g., informed pulses and/or control pulses that may or may not contribute to therapy for the patient) are based on comparing the value of a characteristic of a measured ECAP signal to a target ECAP characteristic value. In response to delivering a control pulse defined by a set of stimulation parameter values, IMD 110, via two or more electrodes interposed on leads 108, senses electrical potential of tissue of the spinal cord 106 of patient 102 to measure the electrical activity of the tissue. IMD 110 senses ECAP from the target tissue of patient 102, e.g., with electrodes on one or more leads 108 and associated sense circuitry. In some examples, IMD 110 may receive a sensor signal indicative of the ECAP from one or more sensors, e.g., one or more electrodes and circuitry, internal or external to patient 102. Such an example signal may include a sensor signal indicating an ECAP of the tissue of patient 102. Examples of the one or more sensors include one or more sensors configured to measure a compound action potential of patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, or a sensor configured to detect a respiratory function of patient 102. In some examples, external programmer 150 may receive a sensor signal indicating a compound action potential in the target tissue of patient 102 and may transmit a notification of the sensor signal to IMD 110.

In the example of FIG. 1, IMD 110 is described as performing a plurality of processing and computing functions. However, external programmer 150 instead may perform one, several, or all of these functions. In this example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more stimulation parameter that defines the electrical stimulation informed pulses and, in some examples, control pulses, delivered to patient 102.

In some examples, system 100 may change the target ECAP characteristic value and/or growth rate(s) over a period of time, such as according to a change to a stimulation threshold (e.g., a perception threshold or detection threshold specific for the patient). System 100 may be programmed to change the target ECAP characteristic in order to adjust the intensity of informed pulses (e.g., governed therapy) to provide varying sensations to the patient (e.g., increase or decrease the volume of neural activation). Although system 100 may change the target ECAP characteristic value, received ECAP signals may be used by system 100 to adjust one or more parameter values of the informed pulses and/or control pulses in order to meet the target ECAP characteristic value.

One or more devices within system 100, such as, for example, IMD 110 and/or external programmer 150, may perform various functions as described herein. For example, IMD 110 may include stimulation generation circuitry configured to deliver electrical stimulation, sensing circuitry configured to sense a plurality ECAP signals, and processing circuitry. The processing circuitry may be configured to control the stimulation generation circuitry to deliver a plurality of electrical stimulation pulses (e.g., one or more control pulses) having different amplitude values and control the sensing circuitry to detect, after delivery of each electrical stimulation pulse of the plurality of electrical stimulation pulses, a respective ECAP signal of the plurality of ECAP signals.

In some examples, reference may be made to one or more electrodes of IMD 110 "delivering" therapy. In these instances, stimulation generation circuitry of IMD 110 may be connected to one or more electrodes 132 and configured to deliver the therapy "using" or "on" one or more electrodes 132. In some examples described herein, reference may be made to one or more electrodes 132 of IMD 110 "sensing" ECAP signals. In these instances, sensing circuitry of IMD 110 may be connected to one or more electrodes 132 and configured to sense the ECAP signals "using" or "on" one or more electrodes 132. A different set (e.g., pair) of one or more electrodes 132 may be used for delivering therapy than a set (e.g., pair) of one or more electrodes 132 may be used for sensing ECAP signals. While the above refers to ECAP signals, similar techniques may be used for other sensing signals. In some examples, reference may be made to certain recharge states (e.g., active recharge or passive recharge) as "on" one or more electrodes 132 of IMD 110. In these instances, circuitry connected to one or more electrodes 132 may be "in" the certain recharge state.

In the example of FIG. 1, IMD 110 is described as performing a plurality of processing and computing functions. However, external programmer 150 instead may perform one, several, or all of these functions. In this example, IMD 110 may relay sensed signals to external programmer 150 for analysis and external programmer 150 may transmit instructions to IMD 110 to adjust the one or more parameters defining the electrical stimulation signal based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more parameters that define the electrical stimulation signal.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitude values. Therefore, electrical stimulation in the form of a non-pulse signal may be a continuous signal that may have a sinusoidal waveform or other continuous waveform.

In some examples, sensing circuitry of IMD 110 may be coupled to control electrodes of one or more electrodes 132 and governing electrodes of one or more electrodes 132. The control electrodes may be configured to deliver control pulses to patient tissue that elicit ECAP signals from the tissue of patient 102. The governing electrodes may be configured to deliver governed therapy (e.g., informed pulses) to patient tissue that provide therapy to patient 102. The sensing circuitry may include one or more amplifiers configured to amplify ECAP signals within the circuitry for more accurate sensing of the ECAP signals. The sensing circuitry may also include processing circuitry configured to enter an active recharge state on the control electrodes and, subsequent to entering an active recharge state, enter a passive recharge state on the control electrodes. The active recharge state and passive recharge state are explained with more specificity below.

Figure 2:
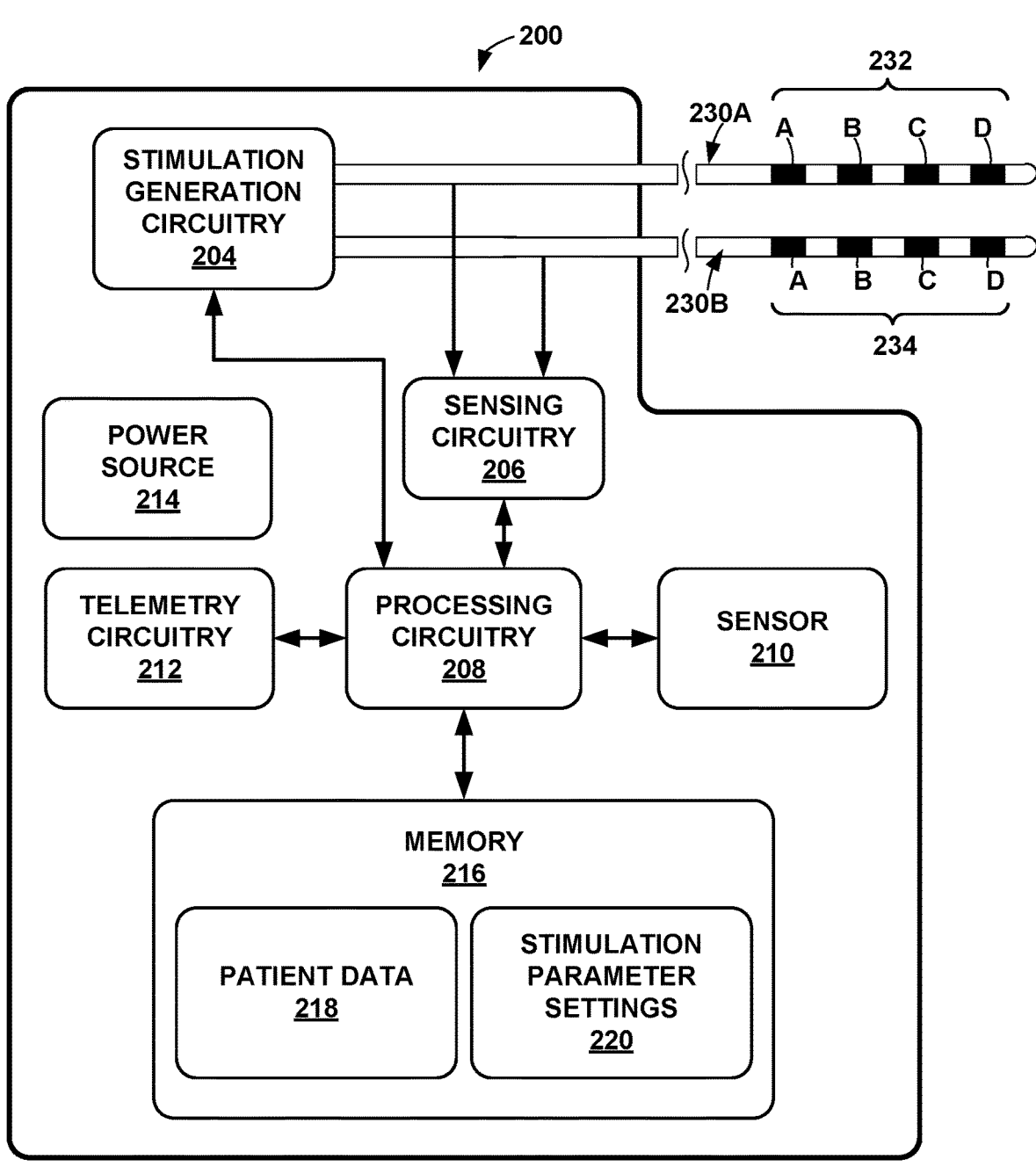
FIG. 2 is a block diagram of the example IMD of FIG. 1, in accordance with one or more techniques of this disclosure.

FIG. 2 is a block diagram of the example IMD of FIG. 1. IMD 200 may be an example of IMD 110 of FIG. 1. In the example shown in FIG. 2, IMD 200 includes stimulation generation circuitry 204, sensing circuitry 206, processing circuitry 208, sensor 210, telemetry circuitry 212, power source 214, and memory 216. Each of these circuits may be or include programmable or fixed function circuitry can perform the functions attributed to respective circuitry. For example, processing circuitry 208 may include fixed-function or programmable circuitry, stimulation generation circuitry 204 may include circuitry can generate electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 may store patient data 218, which may include anything related to the patient such as one or more patient postures, an activity level, or a combination of patient posture and activity level. Patient data 218 may store, for each patient posture, one or more propagation characteristics. For example, patient data 218 may store, for each patient posture, one or more of a first conduction velocity of the tissue for a first ECAP signal of a set of ECAP signals that is responsive to a first phase of a stimulation pulse generated by stimulation generation circuitry 204, a second conduction velocity of the tissue for a second ECAP signal of the set of ECAP signals that is responsive to the second phase of the stimulation pulse generated by stimulation generation circuitry 204, a time delay between the first ECAP signal and the second ECAP signal, a first launch time between a calculated propagation time the first ECAP signal and a measured propagation time for the first ECAP signal, or a second launch time between a calculated propagation.

Memory 216 may store stimulation parameter settings 220 within memory 216 or separate areas within memory 216. Each stored stimulation parameter setting 220 defines values for one or more sets of electrical stimulation parameters (e.g., an informed stimulation parameter set and a control stimulation parameter set, or parameters for other pulse trains). Stimulation parameter settings 220 may also include additional information such as instructions regarding delivery of electrical stimulation signals based on stimulation parameter relationship data, which can include relationships between two or more stimulation parameters based upon data from electrical stimulation signals delivered to patient 102 or data transmitted from external programmer 104. The stimulation parameter relationship data may include measurable aspects associated with stimulation, such as an ECAP characteristic value.

Accordingly, in some examples, stimulation generation circuitry 204 may generate electrical stimulation signals (e.g., informed pulses and/or control pulses) in accordance with the electrical stimulation parameters noted above. Other ranges of stimulation parameter values may also be useful and may depend on the target stimulation site within patient 102. While stimulation pulses are described, stimulation signals may be of any form, such as continuous-time signals (e.g., sine waves or cosine waves) or the like.

Sensing circuitry 206 may be configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP. In some examples, sensing circuitry 206 detects ECAP from a particular combination of electrodes 232, 234. In some examples, the particular combination of electrodes for sensing ECAP includes different electrodes than a set of electrodes 232, 234 used to deliver control stimulation pulses and/or informed stimulation pulses. In some examples, the particular combination of electrodes used for sensing ECAP includes at least one of the same electrodes as a set of electrodes used to deliver informed and/or control stimulation pulses to patient 102. Sensing circuitry 206 may provide signals to an analog-to-digital converter (ADC), for conversion into a digital signal for processing, analysis, storage, or output by processing circuitry 208.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry can provide the functions attributed to processing circuitry 208 herein may be embodied as firmware, hardware, software, or any combination thereof. Processing circuitry 208 may control stimulation generation circuitry 204 to generate electrical stimulation signals according to stimulation parameter settings 220 stored in memory 216 to apply stimulation parameter values, such as, for example, a pulse amplitude value, a pulse width, a pulse frequency, and/or a waveform shape of each of the electrical stimulation signals.

In the example of FIG. 2, set of electrodes 232 includes electrodes 232A, 232B, 232C, and 232D, and the set of electrodes 234 includes electrodes 234A, 234B, 234C, and 234D. In some examples, a single lead may include all eight electrodes 232 and 234 along a single axial length of the lead. Each electrode combination of electrodes 232 may have a respective spatial separation. In some examples, patient data 218 may store, for each pair of electrodes of electrodes 223, a respective spatial separation. Processing circuitry 208 may determine a propagation parameter based on the spatial separation of electrodes 232. For example, processing circuitry 208 may determine a spatial delay between electrodes 232A and 234A based on the spatial separation of electrodes 232A and 234A and one or more of a first conduction velocity for a cathodic phase of a stimulation pulse generated by stimulation generation circuitry 204 or a second conduction velocity for an anodic phase of the stimulation pulse generated by stimulation generation circuitry 204.

Processing circuitry 208 also controls stimulation generation circuitry 204 to generate and apply the electrical stimulation signals to selected combinations of electrodes 232, 234. In some examples, stimulation generation circuitry 204 includes a switch circuit that may couple stimulation signals to selected conductors within leads 230, which, in turn, may deliver the stimulation signals across selected electrodes 232, 234. Such a switch circuit may be a switch array, switch matrix, multiplexer, or any other type of switch circuitry can selectively couple stimulation energy to selected electrodes 232, 234 and to selectively sense bioelectrical neural signals of a spinal cord of the patient (not shown in FIG. 2) with selected electrodes 232, 234.

As shown, stimulation generation circuitry 204 may not include a switch circuit. In these examples, stimulation generation circuitry 204 may include a plurality of pairs of voltage sources, current sources, voltage sinks, or current sinks connected to each of electrodes 232, 234 such that each pair of electrodes has a unique signal circuit. In other words, in these examples, each of electrodes 232, 234 may be independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 204 via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 204 and processing circuitry 208 in FIG. 2, in some examples, sensing circuitry 206 may be in a separate housing from IMD 200 and may communicate with processing circuitry 208 via wired or wireless communication techniques.

In some examples, one or more of electrodes 232 and 234 may be suitable for sensing ECAP. For instance, electrodes 232 and 234 may sense the voltage amplitude of a portion of the ECAP signals, where the sensed voltage amplitude is a characteristic the ECAP signal.

Memory 216 may be configured to store information within IMD 200 during operation. Memory 216 may include a computer-readable storage medium or computer-readable storage device. In some examples, memory 216 includes one or more of a short-term memory or a long-term memory. Memory 216 may include, for example, random access memories (RAM), dynamic random-access memories (DRAM), static random-access memories (SRAM), magnetic discs, optical discs, flash memories, or forms of electrically programmable memories (EPROM) or electrically erasable and programmable memories (EEPROM). In some examples, memory 216 is used to store data indicative of instructions for execution by processing circuitry 208. As discussed herein, memory 216 can store patient data 218, stimulation parameter settings 220, and control policy data 224.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity. Sensor 210 may include one or more accelerometers, optical sensors, chemical sensors, temperature sensors, pressure sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210 may indicate a posture state (e.g., sleeping, awake, sitting, standing, or the like), and processing circuitry 208 may select target and/or threshold ECAP characteristic values according to the indicated posture state.

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as an amplitude value and/or an electrode combination (e.g., for informed and/or control pulses), from the external programmer via telemetry circuitry 212. Updates to stimulation parameter settings 220 and input efficacy threshold settings 226 may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 may deliver operating power to various components of IMD 200. Power source 214 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power consumption levels when needed to extend the operating time of power source 214.

Stimulation generation circuitry 204 of IMD 200 may receive, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP signal that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAP recorded at sensing circuitry 206. While the above discussion refers to an ECAP signal, some examples, may be directed to other sensing signals.

In accordance with the techniques of the disclosure, processing circuitry 208 may be configured to determine a propagation characteristic for a set of ECAP signals that are responsive to a stimulation pulse provided by stimulation generation circuitry 204. For example, processing circuitry 208 may determine a time delay between a first ECAP signal that is responsive to a cathodic phase of the stimulation pulse and a second ECAP signal that is responsive to a anodic phase of the stimulation pulse. Processing circuitry 208 may output an indication of the determined propagation characteristic to patient 102 and/or a caretaker of patient 102. In this way, patient 102 or the caretaker of patient 102 may more quickly and more accurately configure program parameters (e.g., a pulse width, an interval between the cathodic phase and the anodic phase, or select electrodes) based on the determined propagation characteristic (e.g., the time delay) compared to systems that do not determine a propagation parameter. While this example describes the propagation characteristic as a time delay, the propagation characteristic may additionally or alternatively include other information, such as, for example, a conduction velocity or a launch time as described further below.

Moreover, in some examples, processing circuitry 208 or another device of system 100 may determine the program parameters based on the propagation characteristic without user input. Processing circuitry 208 may then apply the determined program parameters with or without user input (e.g., a confirmation input). For instance, processing circuitry 208 may store the determined program parameters in stimulation parameter settings 220 and provide therapy using the determined program parameters stored in stimulation parameter settings 220.

Figure 3:
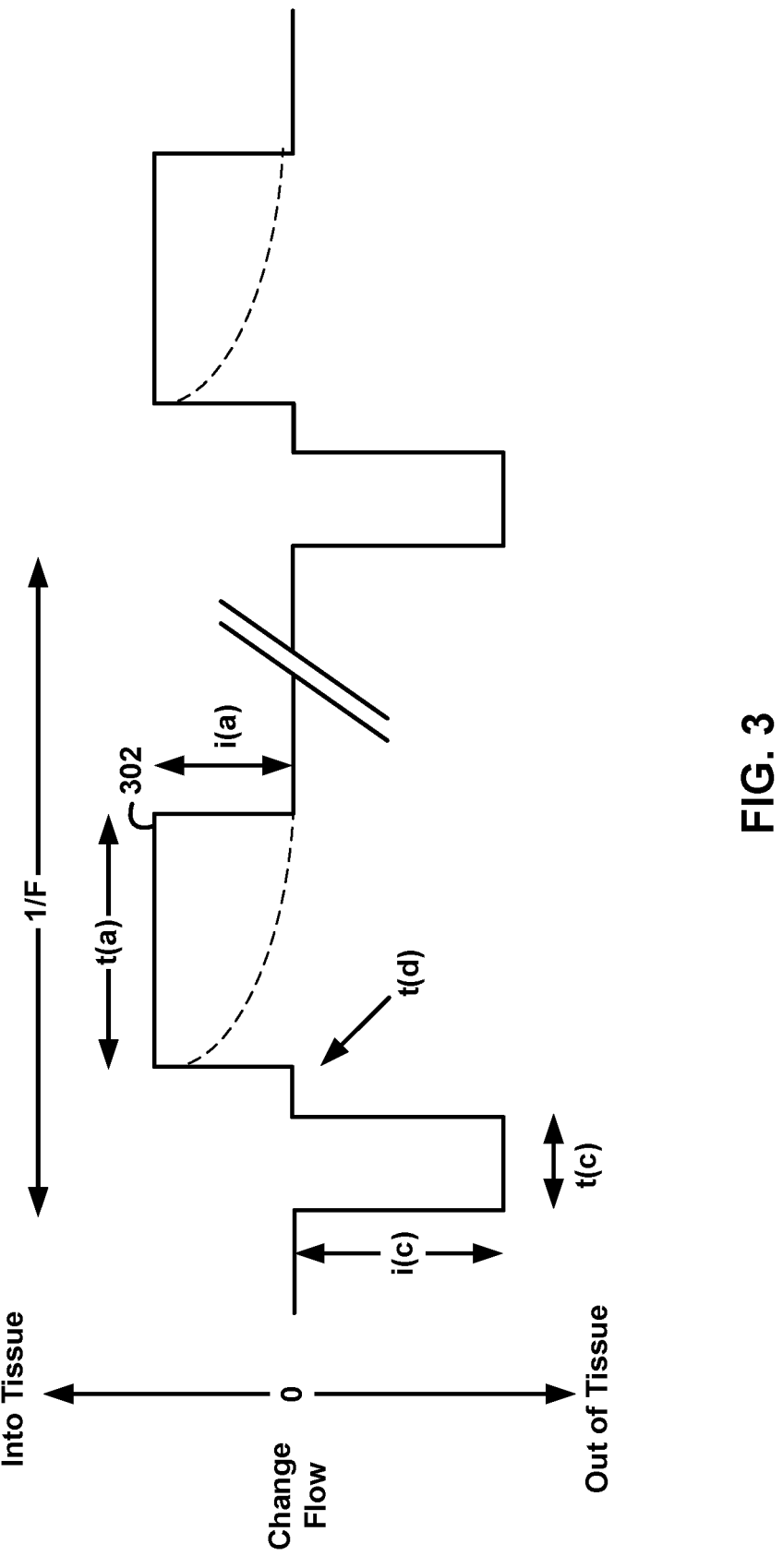
FIG. 3 is a conceptual diagram illustrating an example stimulation pulse, in accordance with one or more techniques of this disclosure.

FIG. 3 is a conceptual diagram illustrating an example stimulation pulse, in accordance with one or more techniques of this disclosure. The abscissa axis of FIG. 3 represents time and the ordinate axis of FIG. 3 represents a charge flow 302 into tissue (e.g., positive charge flow) or out of tissue (e.g., negative charge flow). Charge flow 302 may represent an example stimulation pulse, where i(c) is cathodic charge flow out of the tissue (e.g., a cathodic phase of the stimulation pulse), t(c) is the duration of the cathodic charge flow, t(d) is the interval between cathodic and anodic phases, i(a) is the anodic charge flow into the tissue (e.g., an anodic phase of the stimulation pulse), t(a) is the duration of the anodic charge flow, and F is the frequency of charge delivery. The solid line for i(a) indicates "active" anodic recharge versus the "passive" recharge illustrated with the dotted line. The pulse of FIG. 3 is a biphasic pulse which is an example of multiphasic pulses. However, a triphasic pulse or other pulse may be used in other examples in which one or more anodic phases are combined with one or more cathodic phases in the single multiphasic pulse.

While monophasic neurostimulation may be used for intermittent or infrequent applications, chronic neurostimulation can employ multiphasic (e.g., biphasic or triphasic) stimulation to avoid the formation of deleterious reaction products and tissue damage at the electrode-tissue interface. For biphasic stimulation, for example, at least a first electrode acts as an electrochemical cathode while at least a second electrode acts as an electrochemical anode for a first phase. After a brief interval (e.g., zero or more than zero) referred to herein as the interphase interval (IPI), the role of the electrodes may be reversed and what was previously the cathode becomes the anode, and vice versa.

For cathodic stimulation (e.g., a first phase of the stimulation pulse), a flow of electric current is out of tissue (e.g., a neural target) and current is sunk from the tissue. Electrons are emitted by the cathode into the tissue, cations are reduced, and the potential of the cathode with respect to the anode falls. FIG. 3 represents cathodic stimulation during the duration (t(c)) when the cathodic charge flows out of the tissue (i(c)). During the interphase interval between cathodic and anodic phases (t(d)) there is zero or near-zero flow of electrical current into/out of the tissue.

For anodic stimulation (e.g., a second phase of the stimulation pulse), the flow of electric current is into tissue (e.g., a neural target) and current is sourced into the tissue. Electrons are collected by the anode, cations are formed, and the potential of the anode with respect to the cathode rises. FIG. 3 represents anodic stimulation during the duration (t(a)) when the anodic charge flows out of the tissue (i(ac)).

The cathode during the first phase of a biphasic stimulation complex can serve as the locus of action potential initiation and may have the morphology of a square pulse, although many different morphologies are possible. The second phase may have a morphology that is the same as, or differs from, the first phase. The second phase may be further classified by whether the stimulation circuitry actively drives current through the tissue ("active recharge") or relies on the passive discharge of charge through series capacitors ("passive recharge").

Figure 4A:
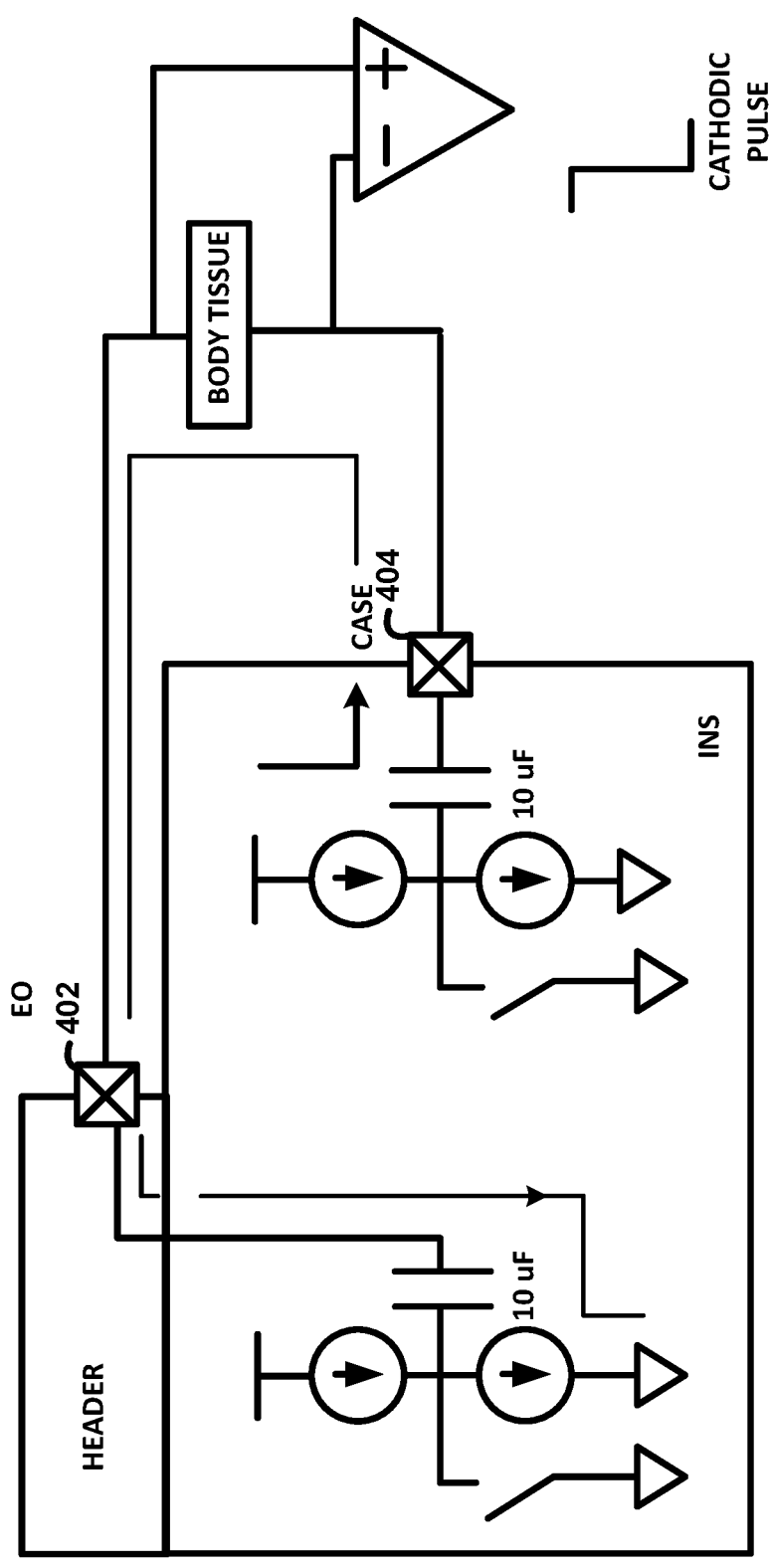
FIG. 4A is a conceptual diagram illustrating an example circuit for providing a cathodic pulse in the spine of a patient, in accordance with one or more techniques of this disclosure.

FIG. 4A is a conceptual diagram illustrating an example circuit for providing a cathodic pulse in the spine of a patient, in accordance with one or more techniques of this disclosure. FIG. 4A represents an example circuit 400 configuration used to deliver active recharge and passive recharge. The examples of FIGS. 4A-4D are directed to a spinal cord stimulator where cathodic stimulation is desired at electrode zero (E0) 402 with respect to case 404 of an implantable neurostimulator (INS). For the first phase in the example of FIG. 4A, case 404 would be configured as the "+" terminal and act as the anode. Current enters the anode, and electrons are subsequently collected owing to the oxidation reactions occurring at the anode. E0 402 is configured as the "−" terminal and acts as the electrochemical cathode. Current exits the cathode, and electrons are subsequently emitted owing to the reduction reactions occurring at the cathode. If the body tissue being stimulated is observed differentially with respect to the INS case, a negative voltage (the cathodic pulse) may develop which is a function of the applied current and the resistance through the body tissue from E0 402 to case 404. Current is sunk from the spine into E0 402.

Figure 4B:
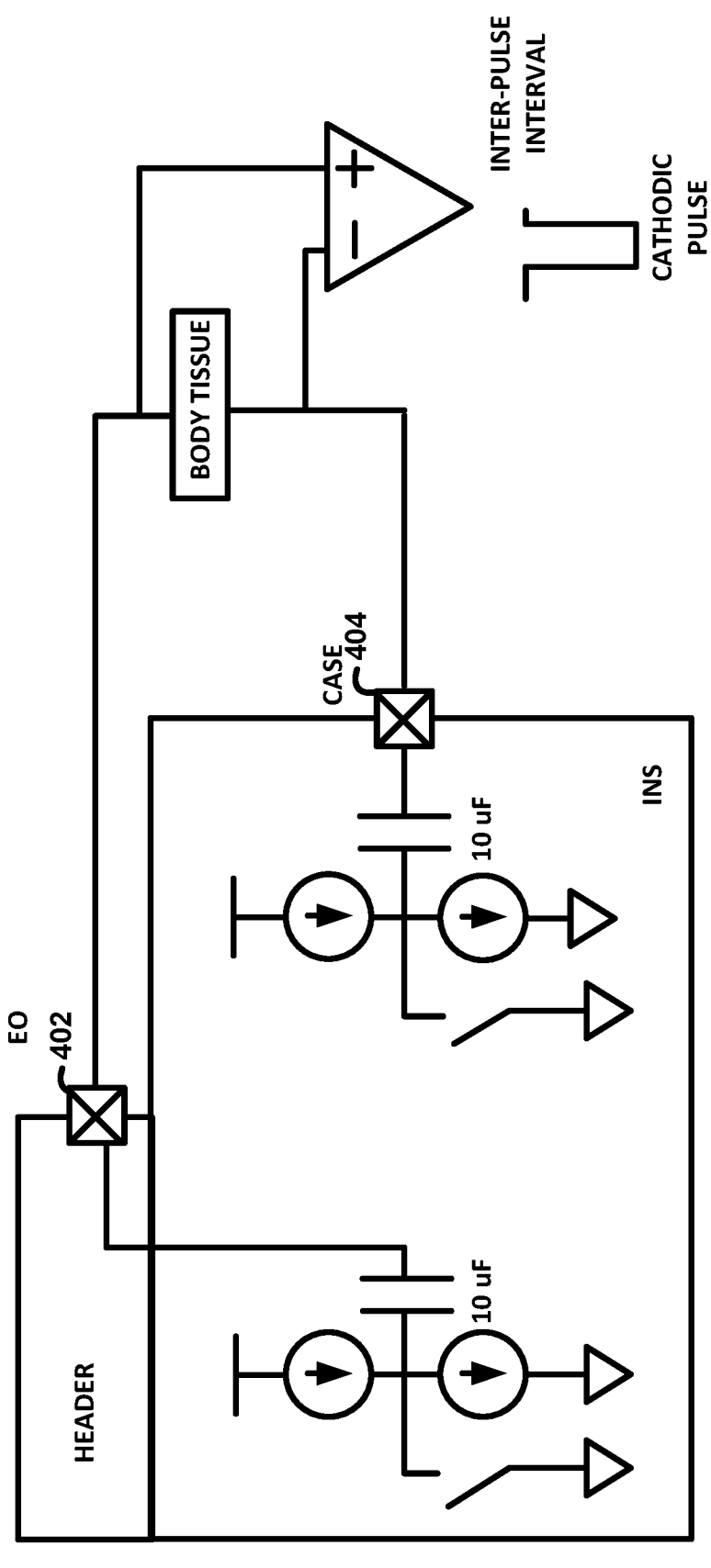
FIG. 4B is a conceptual diagram illustrating the example circuit of FIG. 4A during an interphase interval, in accordance with one or more techniques of this disclosure.

FIG. 4B is a conceptual diagram illustrating the example circuit of FIG. 4A during an interphase interval, in accordance with one or more techniques of this disclosure. After the cathodic pulse is delivered, no current is sourced through the body during the IPI. If the body tissue is modeled as a pure resistor, no voltage is seen across the body tissue as shown in FIG. 4B.

Figure 4C:
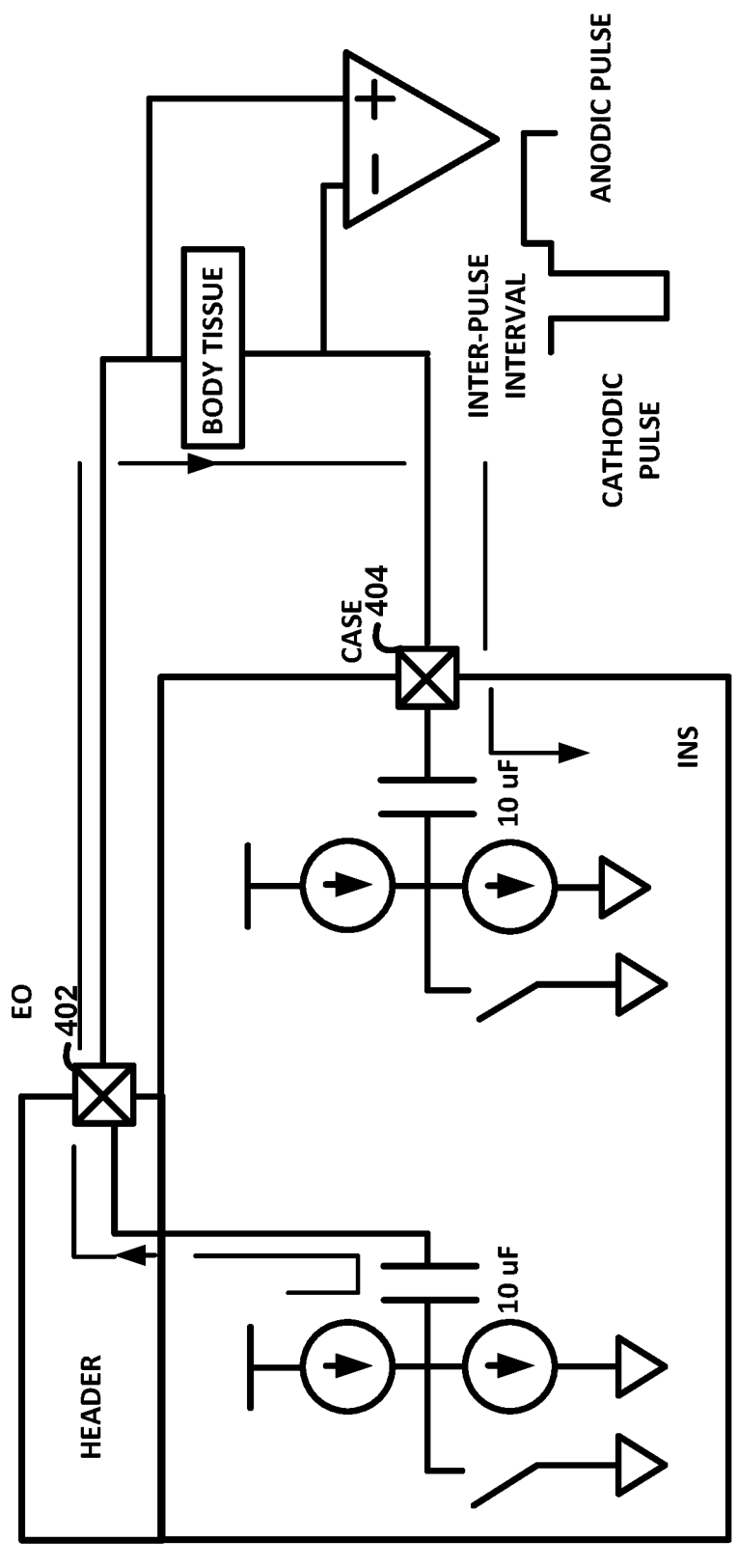
FIG. 4C is a conceptual diagram illustrating the circuit of FIG. 4A providing an anodic pulse in the spine of a patient, in accordance with one or more techniques of this disclosure.

FIG. 4C is a conceptual diagram illustrating the circuit of FIG. 4A providing an anodic pulse in the spine of a patient, in accordance with one or more techniques of this disclosure. After delivering the cathodic pulse and waiting for the IPI, current is driven in the opposite direction through the body tissue to reverse potentials developed on the coupling capacitors and the electrodes. As described above, two means to accomplish this are active or passive recharge. A combination of active and passive recharge may also be used. For active recharge, an anodic pulse is delivered into the body tissue following the IPI. E0 402 now sources current and becomes the anode. Case 404 sinks current and becomes the cathode.

Figure 4D:
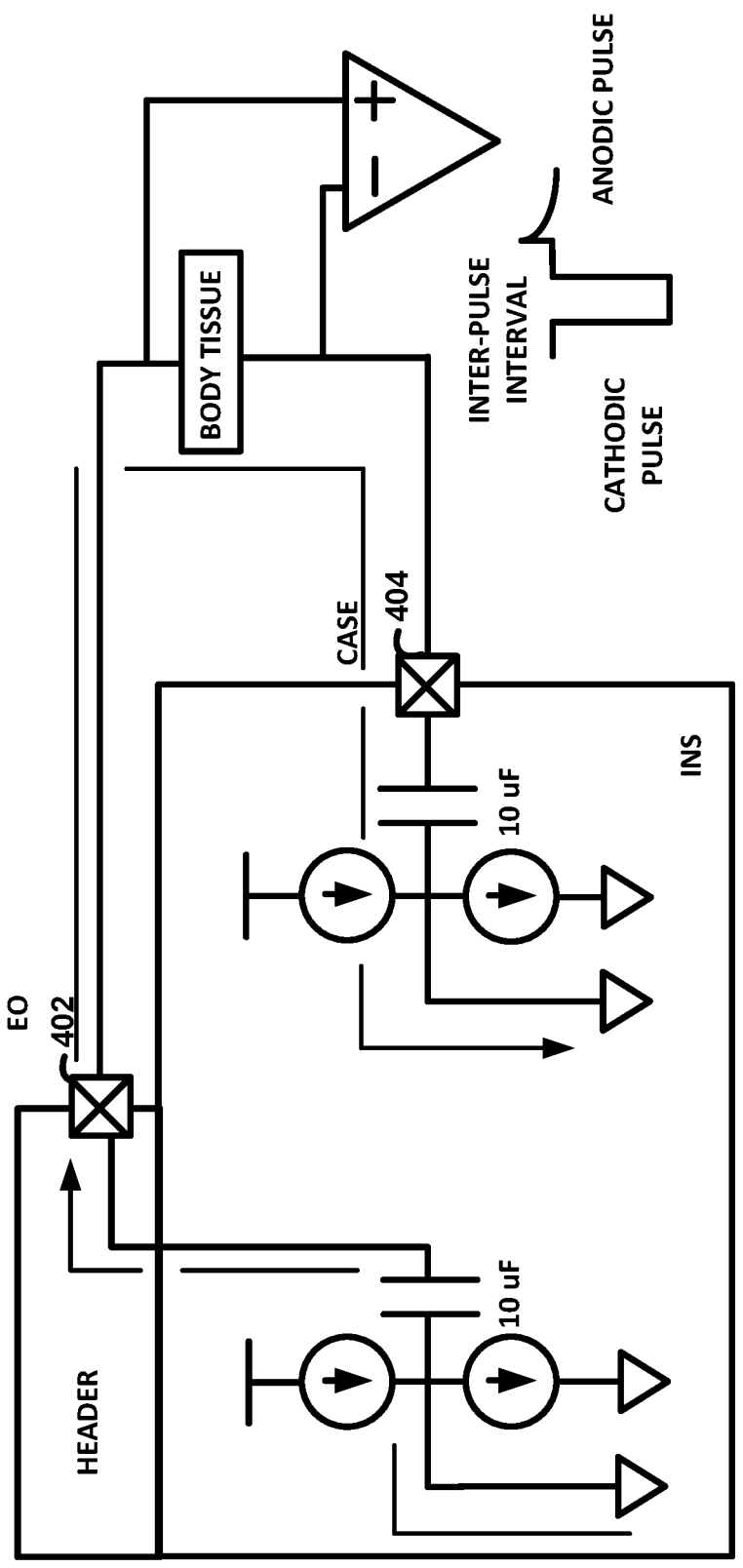
FIG. 4D is a conceptual diagram illustrating the circuit of FIG. 4A during a passive recharge, in accordance with one or more techniques of this disclosure.

FIG. 4D is a conceptual diagram illustrating the circuit of FIG. 4A during a passive recharge, in accordance with one or more techniques of this disclosure. For passive recharge, as shown in FIG. 4D, the two grounding switches between the current sinks and sources close and the voltage developed across capacitors is allowed to dissipate through the body tissue back to steady-state conditions.

Figure 5:
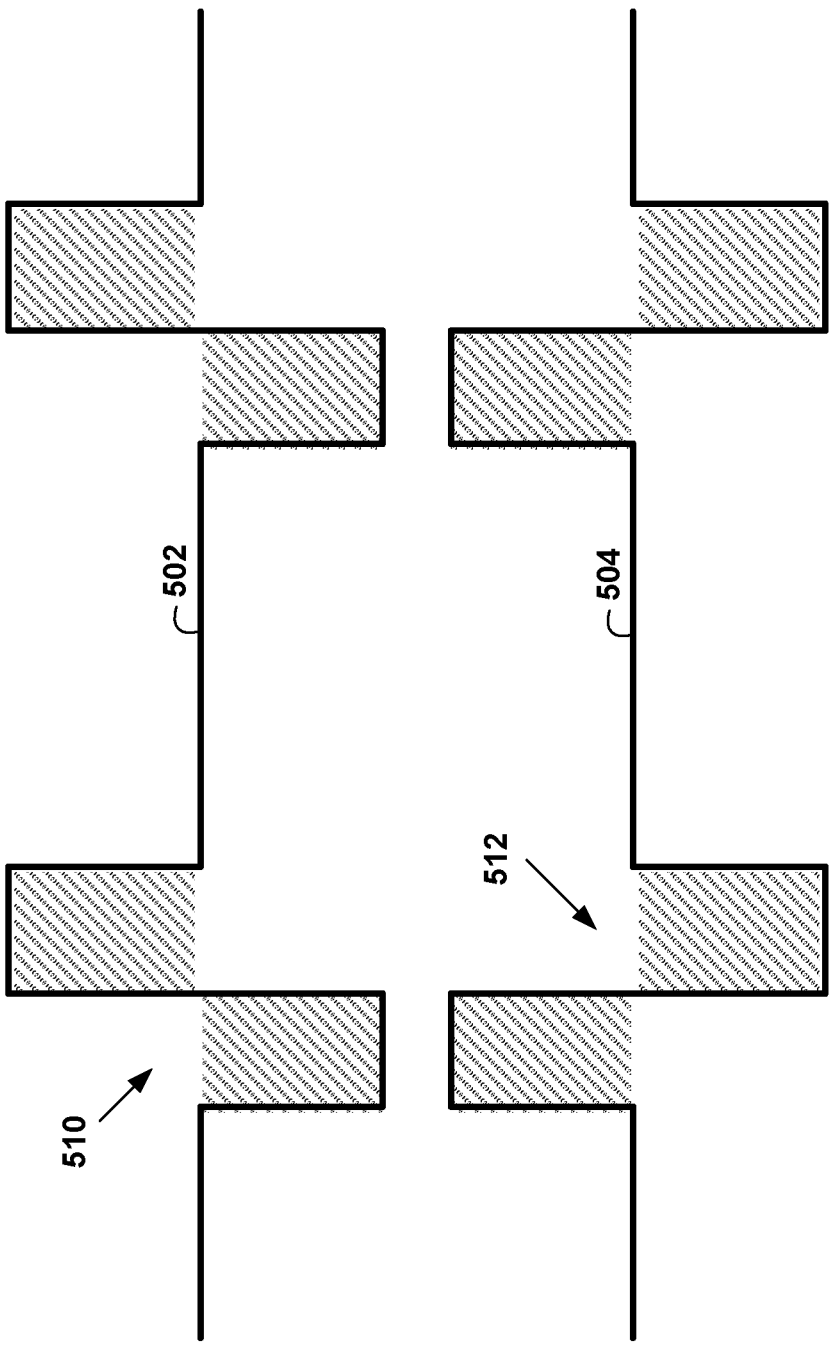
FIG. 5 is a timing diagram illustrating an example voltage potentials of multi-polar stimulation to control a distance between two potential stimulation sites, in accordance with one or more techniques of this disclosure.

FIG. 5 is a timing diagram illustrating an example voltage potentials of multi-polar stimulation or "virtual bi-pole" to control a distance between two potential stimulation sites, in accordance with one or more techniques of this disclosure. For example, IMD 110 may adjust the precise distance between stimulation sites to match the speed of conduction of a particular person. The abscissa axis of FIG. 5 represents time and the ordinate axis of FIG. 5 represents a first voltage potential 502 at a first stimulation electrode and a second voltage potential 504 at a second stimulation electrode with respect to each other for biphasic stimulation. As shown during a first negative excitation phase (510), the first stimulation electrode acts as the cathode and the second stimulation electrode acts as the anode. During a second negative excitation phase (512), the first stimulation electrode acts as the anode and the second stimulation electrode acts as the cathode.

Although biphasic pulses are described in the example of FIG. 5, other multiphasic pulses, such as a triphasic pulse, may be used in other examples. An ECAP signal may be elicited by some or all phases of the multiphasic pulse, and the timing between any of these ECAP signals may be identified to determine a propagation characteristic as described herein. A triphasic pulse may typically have a first phase of a first polarity, followed by a second phase of a second polarity, followed by a third phase of the first polarity. Typically, the total charge delivered at the first polarity would be approximately equal and opposite to the total charge delivered at the second polarity. In some examples, the third phase may be a passive recharge phase.

In some examples, such as when active recharge is used and the second phase of stimulation is equal and opposite to the first phase, a second wavefront of action potentials may be launched coincident with the second phase. As discussed above, this behavior may occur because the role of the electrodes as either cathode or anode reverses during the second phase of stimulation. Further, during the second phase, the population of fibers excited during the first phase is (a) capable of being excited by the second phase (e.g., is not in an absolute refractory state) and/or (b) differs anatomically from those excited by the second phase. Regarding point (b), one set of fibers might be carrying an action potential initiated by the first phase while a second set might be carrying an action potential initiated from the second phase. The superposition of all the action potentials launched from the stimulation complex is the ECAP that can be measured with electrodes in the epidural space of the spinal cord (e.g., when the intended application is spinal cord stimulation and sensing).

In response to stimulation generation circuitry 204 generating first voltage potential 502 at a first electrode and second voltage potential 504 at a second electrode during the first phase of a stimulation pulse, a first ECAP signal may be generated in tissue of patient 102. The first ECAP signal may be generated by the leading edge of the $1^{st}$ negative excitation phase illustrated in FIG. 5. Similarly, in response to stimulation generation circuitry 204 generating first voltage potential 502 at a first electrode and second voltage potential 504 at a second electrode during the second phase of the stimulation pulse, a second ECAP signal may be generated in tissue of patient 102. The second ECAP signal may be generated by the leading edge of the $2^{nd}$ negative excitation phase illustrated in FIG. 5. Neural activation may be delayed somewhat with respect to the leading edge until enough charge is delivered to the neural target. The first ECAP signal and the second ECAP signal can be linearly superimposed in time (e.g., because the first ECAP signal and the second ECAP signal mat propagate on different fiber tracts). In some examples, the first ECAP signal (ECAP1) and the second ECAP signal (ECAP 2) may be equal (e.g., ECAP1=ECAP2). The sum of ECAP1 and ECAP2 may be defined as:

$$Vsum(t)=Vecap1(t)+Vecap2(t)=Vecap1(t)+k\times Vecap1$$
$$(t-tdelay)$$

Where:

tdelay is delay of ECAP2 relative to ECAP1 tdelay=t_pulse+t_ipi+/−t_spatial.

t_pulse=pulse width of one phase of excitation pulse t_ipi=interval between phases +/−t_spatial=delay due to spatial separation of negative and positive excitation electrodes. This delay is added to tdelay when 1st negative excitation phase is performed on a more proximal electrode relative to sense electrodes (e.g., stimulation on E0+/E1− with recording on E6/E7) and subtracted if the 1st negative excitation phase is performed on more distal electrode relative to sense electrodes (i.e., stimulation E0−/E1+ with recording on E6/E7).

k=empirical attenuation factor to account for attenuation/amplification of the ECAP as it propagates.

Figure 6:
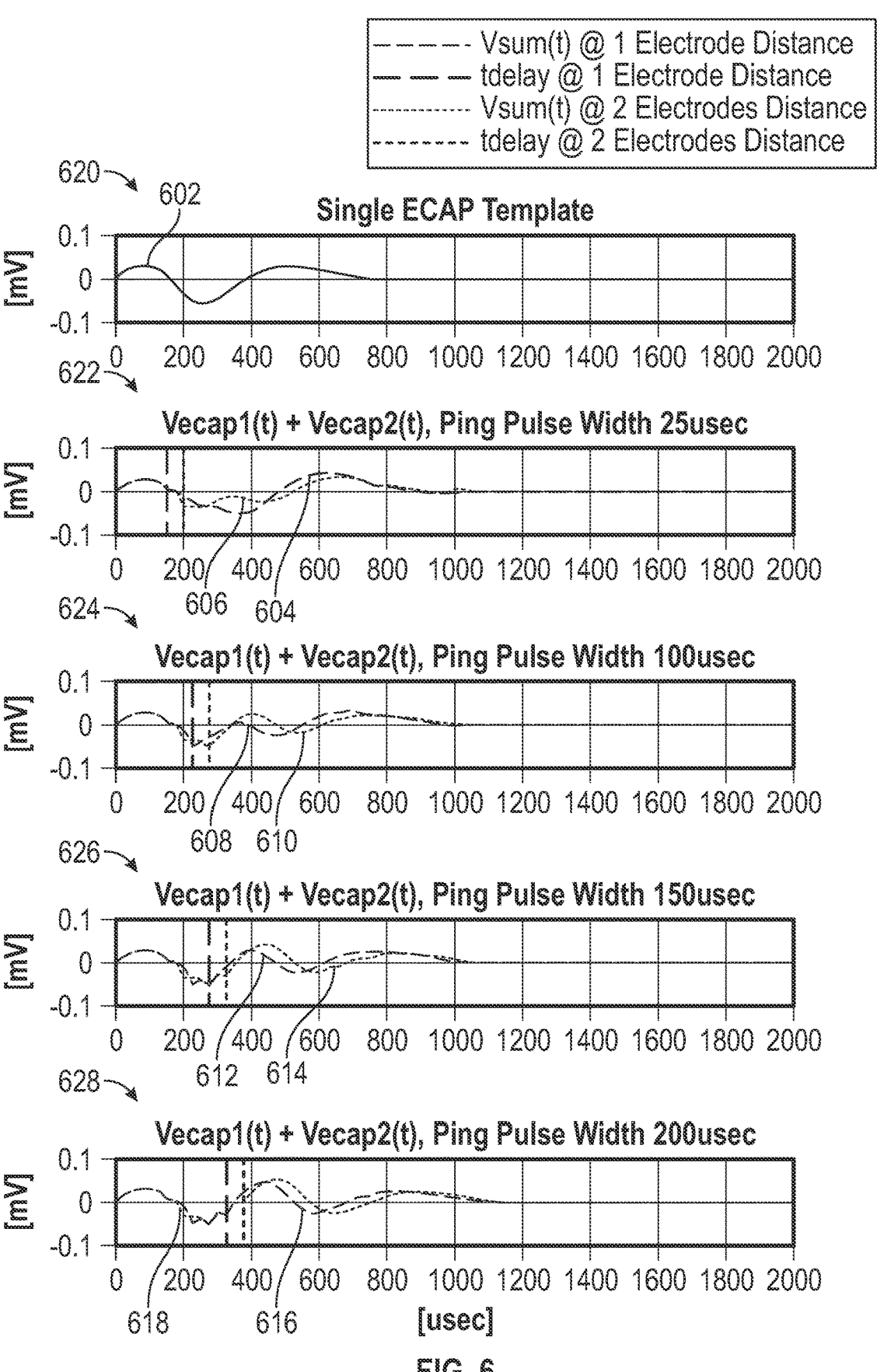
FIG. 6 is a plot diagram illustrating first example summation of evoked action potential (ECAP) signals for different pulse widths, in accordance with one or more techniques of this disclosure.

FIG. 6 is a plot diagram illustrating first example summation of ECAP signals for different pulse widths, in accordance with one or more techniques of this disclosure. The abscissa axis of FIG. 6 represents time and the ordinate axis of FIG. 6 represents a first voltage 602 representing a resulting composite ECAP, a second voltage 604 representing a resulting composite ECAP for a control pulse width of 25 microseconds for a 1 electrode distance, a third voltage 606 representing a resulting composite ECAP for a control pulse width of 25 microseconds for a 2 electrode distance, a fourth voltage 608 representing a resulting composite ECAP for a control pulse width of 100 microseconds for a 1 electrode distance, a fifth voltage 610 representing a resulting composite ECAP for a control pulse width of 100 microseconds for a 2 electrode distance, a sixth voltage 612 representing a resulting composite ECAP for a control pulse width of 150 microseconds for a 1 electrode distance, a seventh voltage 614 representing a resulting composite ECAP for a control pulse width of 150 microseconds for a 2 electrode distance, an eighth voltage 616 representing a resulting composite ECAP for a control pulse width of 200 microseconds for a 1 electrode distance, and a ninth voltage 618 representing a resulting composite ECAP for a control pulse width of 200 microseconds for a 2 electrode distance.

FIG. 6 shows the resultant Vsum(t) for the following simulated test conditions:

ECAP1=ECAP2

First negative phase is delivered on electrode closer to the recording pair; i.e., stimulation on E0+/E1− with recording on E6/E7.

T_ipi=30 μs

An assumed conduction velocity=100 m/s, and electrode pitch=7 mm. t_spatial=+70 μs If stimulation is between adjacent electrodes, and t_spatial=+140 μs if one electrode is skipped.

An assumed k=0.9 for adjacent electrode stimulation (one electrode distance) and 0.8 for skipped electrode stimulation (two electrode distance).

FIG. 6 shows exemplary plots 620-628 with different pulse widths and the first negative phase delivered on the electrode closest to the recording pair (e.g., stimulating on E0+/E1− with recording on E6/E7). Plot 620 shows a first voltage 602 representing a resulting composite ECAP. Plot 622 shows a second voltage 604 representing a resulting composite ECAP for a control pulse width of 25 microseconds for a 1 electrode distance and a third voltage 606 representing a resulting composite ECAP for a control pulse width of 25 microseconds for a 2 electrode distance. Plot 624 shows a fourth voltage 608 representing a resulting composite ECAP for a control pulse width of 100 microseconds for a 1 electrode distance and a fifth voltage 610 representing a resulting composite ECAP for a control pulse width of 100 microseconds for a 2 electrode distance. Plot 626 shows a sixth voltage 612 representing a resulting composite ECAP for a control pulse width of 150 microseconds for a 1 electrode distance and a seventh voltage 614 representing a resulting composite ECAP for a control pulse width of 150 microseconds for a 2 electrode distance. Plot 628 shows an eighth voltage 616 representing a resulting composite ECAP for a control pulse width of 200 microseconds for a 1 electrode distance and a ninth voltage 618 representing a resulting composite ECAP for a control pulse width of 200 microseconds for a 2 electrode distance.

In FIG. 6, P1 from E0 superimposes on N1 from E1 (e.g., particularly evident with the 100 μs stimulation) to suppress the aggregate amplitude of the ECAP. Instead of assuming a triphasic morphology (P1/N1/P2), the ECAP looks polyphasic due to the delayed contribution of N1/P2 from E0.

Figure 7:
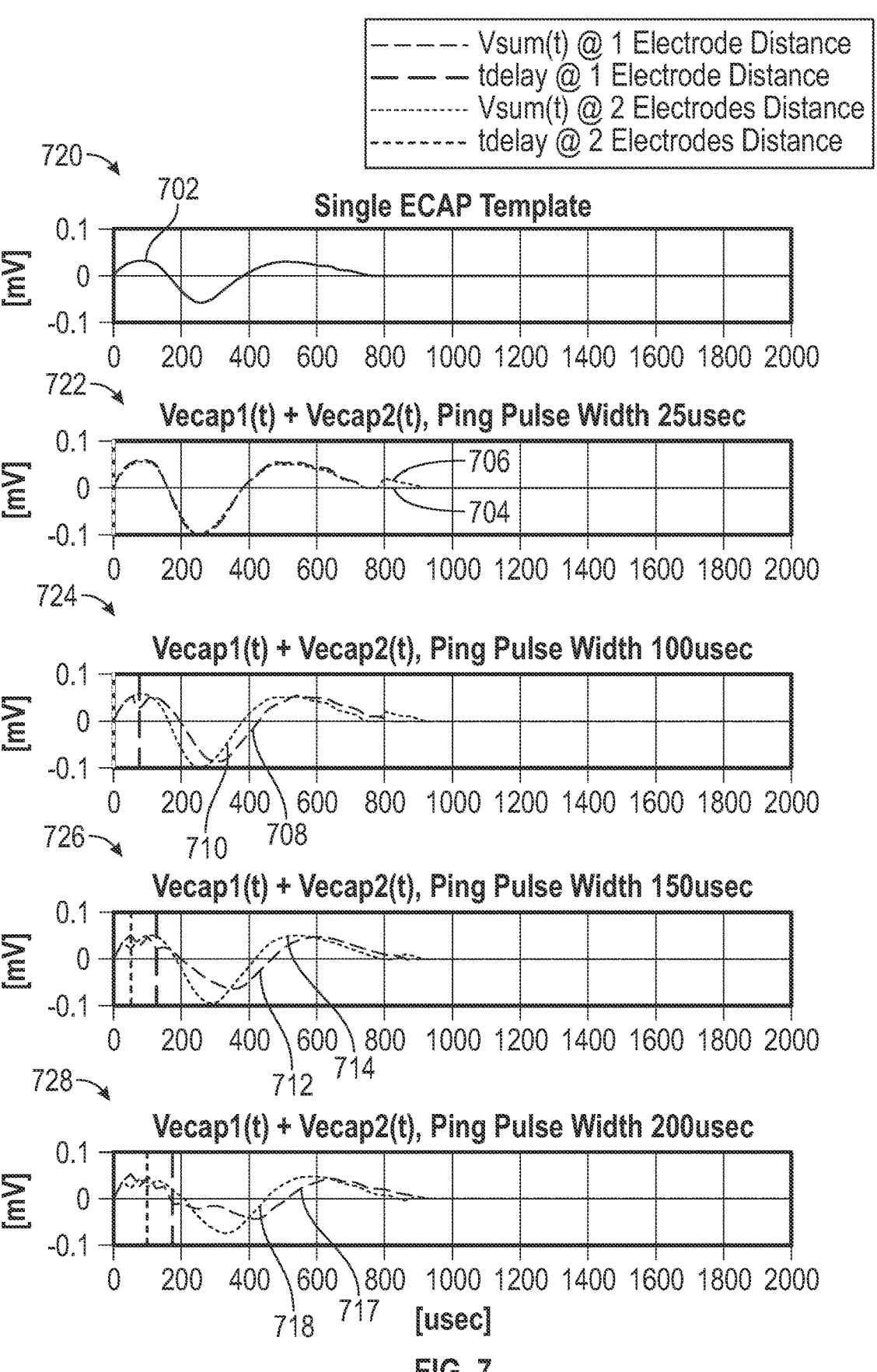
FIG. 7 is a plot diagram illustrating second example summation of ECAP signals for different pulse widths, in accordance with one or more techniques of this disclosure.

FIG. 7 is a plot diagram illustrating second example summation of ECAP signals for different pulse widths, in accordance with one or more techniques of this disclosure. The abscissa axis of FIG. 7 represents time and the ordinate axis of FIG. 7 represents a first voltage 702 representing a resulting composite ECAP for a single ECAP, a second voltage 704 representing a resulting composite ECAP for a control pulse width of 25 microseconds for a 1 electrode distance, a third voltage 706 representing a resulting composite ECAP for a control pulse width of 25 microseconds for a 2 electrode distance, a fourth voltage 708 representing a resulting composite ECAP for a control pulse width of 100 microseconds for a 1 electrode distance, a fifth voltage 710 representing a resulting composite ECAP for a control pulse width of 100 microseconds for a 2 electrode distance, a sixth voltage 712 representing a resulting composite ECAP for a control pulse width of 150 microseconds for a 1 electrode distance, a seventh voltage 714 representing a resulting composite ECAP for a control pulse width of 150 microseconds for a 2 electrode distance, an eighth voltage 716 representing a resulting composite ECAP for a control pulse width of 200 microseconds for a 1 electrode distance, and a ninth voltage 718 representing a resulting composite ECAP for a control pulse width of 200 microseconds for a 2 electrode distance.

The example of FIG. 7 shows the resultant Vsum(t) with the same conditions as above, except:

First negative phase is delivered on electrode furthest from the recording pair; i.e., stimulation on E0−/E1+ with recording on E6/E7.

t_spatial=−70 μs If stimulation is between adjacent electrodes, and t_spatial=−140 μs if one electrode is skipped.

FIG. 7 shows exemplary plots 720-728 with different pulse widths and the first negative phase delivered on the electrode farthest away to the recording pair (e.g., stimulating on E0−/E1+ with recording on E6/E7). Plot 720 shows a first voltage 702 representing a resulting composite ECAP for a single ECAP. Plot 722 shows a second voltage 704 representing a resulting composite ECAP for a control pulse width of 25 microseconds for a 1 electrode distance and a third voltage 706 representing a resulting composite ECAP for a control pulse width of 25 microseconds for a 2 electrode distance. Plot 724 shows a fourth voltage 708 representing a resulting composite ECAP for a control pulse width of 100 microseconds for a 1 electrode distance and a fifth voltage 710 representing a resulting composite ECAP for a control pulse width of 100 microseconds for a 2 electrode distance. Plot 726 shows a sixth voltage 712 representing a resulting composite ECAP for a control pulse width of 150 microseconds for a 1 electrode distance and a seventh voltage 714 representing a resulting composite ECAP for a control pulse width of 150 microseconds for a 2 electrode distance. Plot 728 shows an eighth voltage 716 representing a resulting composite ECAP for a control pulse width of 200 microseconds for a 1 electrode distance and a ninth voltage 718 representing a resulting composite ECAP for a control pulse width of 200 microseconds for a 2 electrode distance.

In FIG. 7, N1 from E0 superimposes on N1 from E1 (particularly evident with the 100 μs stimulation) to enhance the aggregate amplitude of the ECAP. N1-P2 amplitudes are bigger with this case versus the corresponding case in FIG. 6.

Figure 8:
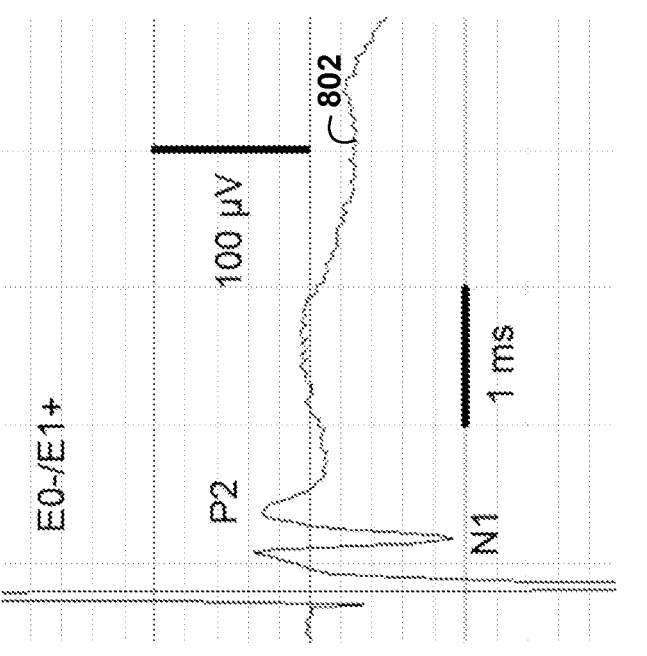
FIG. 8 is a plot diagram illustrating a first composite ECAP signal as measured in sheep, in accordance with one or more techniques of this disclosure.

FIG. 8 is a plot diagram illustrating a first composite ECAP signal as measured in sheep, in accordance with one or more techniques of this disclosure. The abscissa axis of FIG. 8 represents time and the ordinate axis of FIG. 8 represents a composite ECAP signal 802. FIG. 8 is discussed with respect to FIG. 9.

Figure 9:
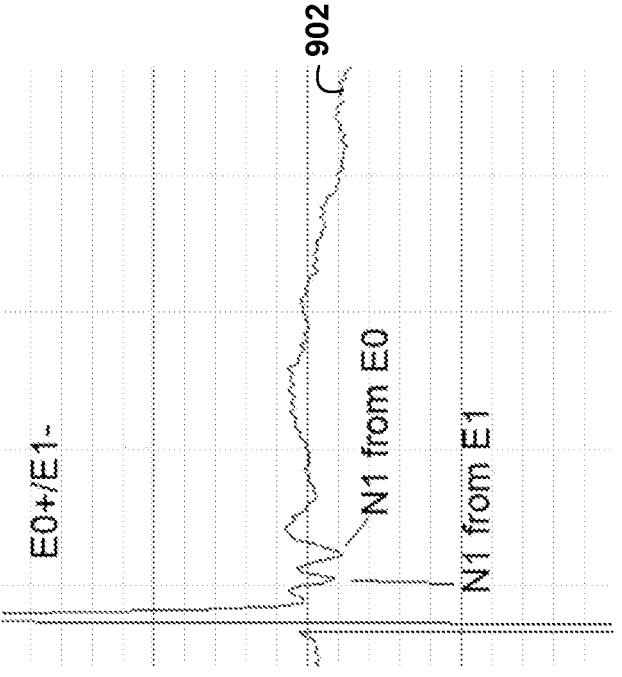
FIG. 9 is a plot diagram illustrating a second composite ECAP signal as measured in sheep, in accordance with one or more techniques of this disclosure.

FIG. 9 is a plot diagram illustrating a second composite ECAP signal as measured in sheep, in accordance with one or more techniques of this disclosure. The abscissa axis of FIG. 9 represents time and the ordinate axis of FIG. 9 represents a composite ECAP signal 902. The data shown in FIGS. 8, 9 are data recorded from a sheep. In both cases, stimulation pulses were delivered at a frequency of 50 Hz on either electrodes E0−/E1+ or E0+/E1−, balanced biphasic pulses at 1.25 mA amplitude (active recharge, 30 μs phase widths) and a 30 μs IPI, and sensing is on electrodes E6/E7. FIG. 8 shows composite ECAP signal 802 resulting from constructive interference from the ECAP signals from respective phases, and FIG. 9 shows composite ECAP signal 902 resulting from destructive interference from the ECAP signals from respective phases in the overall ECAP as measured in sheep.

The examples above all employed active recharge (e.g., a biphasic pulse). However, neurostimulation waveforms with passive recharge may be employed similarly; this may be done to realize the battery referred current savings with passive recharge versus active recharge. Assume for instance that cranial, directional neural enhancement is the desired effect. The following assumptions are used in this example. The conduction velocity of the spinal cord is 50 m/s. Electrode A is configured to deliver a 400 μs stimulation pulse with passive recharge; neural activation is initiated 100 μs (tlaunch_A) after the leading edge of the stimulation pulse. Electrode B is located cranial to electrode A and is configured to deliver a 300 μs stimulation pulse with passive recharge; neural activation is initiated 75 μs (tlaunch_B) after the leading edge of the stimulation pulse. Electrodes A and B are located 5 cm apart; this is a propagation delay (tpropagate) of (5 cm)/(50 m/s)=1 ms. For enhancement, the stimulation pulse can be delivered on electrode B a time (tinterval) later than that on electrode A so the neural activation wavefront launching from B is coincident with the arrival of the wavefront from A. Tinterval=tpropagate+ tlaunch_A−tlaunch_B=1 ms+100 μs−75 μs=1.025 ms.

The above approach may not necessarily result in interference in the opposite direction, as this effect depends on the propagation and launch timings, as well as the morphology of the activation wavefronts.

Techniques described herein may configure a medical device (e.g., IMD 110) to use multiple cathodes to deliver action potentials that either add, or interfere, with each other to result in either directional enhancement or suppression of the evoked compound action potential. While the ECAP may be used to fine tune the timing and characteristics of the stimulation pulses, it is not a requirement.

Stimulation may be delivered with either active or passive recharge. Directional enhancement is accomplished by timing the stimulation pulses and parameters so the two wavefronts are in-phase with each other; suppression is accomplished by configuring parameters and timings are out-of-phase, e.g., the P1 feature from one ECAP overlaps with the N1 feature from another.

A motivation of many motivations for leveraging this physiologic effect stems from the body's inherent response to both synchronized and unsynchronized stimuli. In cochlear implants, for instance, more synchronized stimuli resulting in the patient perceiving a louder sound. In spinal cord stimulation systems, the more synchronized response in FIG. 8 directed cranially may be perceived by a patient as having more paresthesia versus the response in FIG. 9. As such, patients preferring less paresthesia from their stimulation may prefer electrode and stimulation configurations that result in the ECAP of FIG. 8 directed cranially. In another example, a pair of sub-threshold pulses may be delivered that results in a supra-threshold, compound response.

As part of techniques described herein for determining propagation characteristics for ECAP signals, an ECAP signal may be measured to optimize the performance of the system. For example:

ECAPs may be used to assess the conduction velocity of the neural response. IMD 110 may use the conduction velocity for assessing a propagation time (tpropagate), for instance. As an example, a stimulation pulse may be delivered on electrode E7–/E6+ of an octopolar SCS lead (e.g., a lead with eight linear cylindrical electrodes) with ECAP recording on electrodes E2/E1 and E1/E0. The time at a which an ECAP feature, such as peak N1, manifests on both sets of electrodes can be measured and the time difference calculated. IMD 110 may measure the conduction velocity by dividing the time difference into the known electrode spacing (e.g., stored in patient data 218).

IMD 110 may calculate launch times (e.g., tlaunch_A) using ECAP signals. As an example, IMD 110 may calculate conduction velocity using the approach above. Using this information, IMD 110 may calculate the propagation time (tpropagate) as 1 ms between stimulation pair E7–/E6+ and recording pair E1/E0; however, the actual measured interval from the leading edge of the stimulation pulse to the ECAP is 1.1 ms. IMD 110 may infer a launch time of 0.1 ms.

IMD 110 may use ECAP signals to empirically tune the system. For instance, IMD 110 may sweep the pulse widths and/or interval time (tinterval) (e.g., deliver multiple pulses having an incrementally increasing or decreasing pulse width or incrementally increasing or decreasing interval time) until a measured response (i.e., the N1-P2 amplitude) is either maximized or minimized. While these examples are described with respect to IMD 110, in some examples, another device (e.g., external programmer 150 or a cloud-based device) may determine one or more of a conduction velocity or a launch time and/or tune the system.

IMD may use information about the patient (e.g. age and neurological state such as presence of multiple sclerosis) to estimate the conduction velocity from previously available data.

FIG. 10 is a flowchart illustrating an example operation for providing therapy, in accordance with one or more techniques of this disclosure. FIG. 10 is discussed with FIGS. 1-9 for illustration purposes only. Processing circuitry 208 may control the stimulation generation circuitry 204 to deliver the multiphasic stimulation pulse that comprises a first phase and a second phase (1002). For example, processing circuitry 208 may cause stimulation generation circuitry 204 to provide a stimulation pulse shown in FIG. 3. The tissue may comprise, for example, a spinal cord, a peripheral nerve, or a neural tract in the brain. The second phase may provide an active recharge to patient 102. In some examples, the second phase may provide a passive recharge to patient 102.

Processing circuitry 208 may determine, based on the composite ECAP signal, a propagation characteristic for the composite ECAP signal that is elicited by the multiphasic stimulation pulse (1004). Processing circuitry 208 may optionally output an indication of the propagation characteristic (1006). The process shown in FIG. 10 may be repeated, for example, periodically (e.g., every hour, every month) and/or in response to an event (e.g., a change of positional state). For instance, processing circuitry 208 may determine a first propagation characteristic for when patient 102 is in a supine state and a second propagation characteristic for when patient 102 is in a prone state.

For example, processing circuitry 208 may determine a first conduction velocity of the tissue for a first ECAP signal of the composite ECAP signal that is elicited by the first phase. Processing circuitry 208 may determine the first conduction velocity of the tissue based on a time delay between when stimulation generation circuitry 204 provides the multiphasic stimulation pulse to the tissue of patient 102 and when sensing circuitry 206 senses the composite ECAP signal. Processing circuitry 208 may determine a second conduction velocity of the tissue for a second ECAP signal of the composite ECAP signal that is elicited by the second phase.

In some examples, processing circuitry 208 may determine a time delay between the first ECAP signal and the second ECAP signal of the composite ECAP signal. For example, processing circuitry 208 may determine the time delay based on one or more of a pulse width of one or more of the first phase or the second phase, an interval between the first phase and the second phase, or a spatial delay due to a spatial separation between a plurality of electrodes providing the multiphasic stimulation pulse to the tissue. For instance, processing circuitry 208 may determine the time delay based on a summation of the pulse width, the interval, and the spatial delay.

Processing circuitry 208 may determine the spatial delay based on a conduction velocity of the tissue. For example, processing circuitry 208 may determine the conduction velocity of the tissue based on a time delay between when stimulation generation circuitry 204 delivers a reference multiphasic stimulation pulse to the tissue of patient 102 and when sensing circuitry 206 senses a reference composite ECAP signal elicited by the reference multiphasic stimulation pulse and determine the spatial delay using the spatial separation and the conduction velocity.

Processing circuitry 208 may determine a first launch time between a calculated propagation time the first ECAP signal and a measured propagation time for the first ECAP signal. In some examples, processing circuitry 208 may determine a second launch time between a calculated propagation time the second ECAP signal and a measured propagation time for the second ECAP signal. Processing circuitry 208 may determine one or more of the first launch time or the second launch time based on the conduction of velocity of the tissue.

Processing circuitry 208 may optionally cause the stimulation generation circuitry to deliver the therapy to the patient based on the propagation characteristic (1008). The therapy provided by IMD 200 may comprises one or more of spinal cord stimulation (SCS), deep brain stimulation (DBS), peripheral nerve stimulation (PNS), peripheral nerve field stimulation (PNFS), cortical stimulation (CS), pelvic floor stimulation, or gastrointestinal stimulation.

Processing circuitry 208 may apply destructive interference between ECAP signals of the composite ECAP signal resulting from respective phases of the multiphasic stimulation pulse to reduce an amplitude of the composite ECAP signal that is elicited by the multiphasic stimulation pulse. For example, processing circuitry 208 may determine a pulse width of one or more of the first phase or the second phase that minimizes an amplitude of the composite ECAP signal that is elicited by the multiphasic stimulation pulse. Processing circuitry 208 may determine a set of electrodes to deliver the therapy with a spatial separation that minimizes an amplitude of the composite ECAP signal that is elicited by the multiphasic stimulation pulse. Processing circuitry 208 may determine an interval between the first phase and the second phase that minimizes an amplitude of the composite ECAP signal that is elicited by the multiphasic stimulation pulse.

Processing circuitry 208 may apply constructive interference between ECAP signals of the composite ECAP signal resulting from respective phases of the multiphasic stimulation pulse to increase an amplitude of the composite ECAP signal that is elicited by the multiphasic stimulation pulse. For example, processing circuitry 208 may determine a pulse width of one or more of the first phase or the second phase that maximizes an amplitude of the composite ECAP signal that is elicited by the multiphasic stimulation pulse. Processing circuitry 208 may determine a set of electrodes to deliver the therapy with a spatial separation that maximizes an amplitude of the composite ECAP signal that is elicited by the multiphasic stimulation pulse. Processing circuitry 208 may determine an interval between the first phase and the second phase that maximizes an amplitude of the composite ECAP signal that is elicited by the multiphasic stimulation pulse.

In some examples, processing circuitry 208 may determine a target delay between the first phase and the second phase and cause stimulation generation circuitry 204 to provide one or more multiphasic stimulation pulses to the tissue of patient 102 that comprises the first phase of biphasic stimulation and the second phase of the biphasic stimulation with the target delay.

The following examples are examples systems, devices, and methods described herein.

Clause 1: A system comprising: stimulation generation circuitry configured to deliver a multiphasic stimulation pulse to the patient; sensing circuitry configured to sense a composite evoked compound action potential (ECAP) signal elicited by the multiphasic stimulation pulse; and processing circuitry electrically connected to the sensing circuitry and the stimulation generation circuitry, the processing circuitry being configured to: control the stimulation generation circuitry to deliver the multiphasic stimulation pulse that comprises a first phase and a second phase; and determine, based on the composite ECAP signal, a propagation characteristic for the composite ECAP signal that is elicited by the multiphasic stimulation pulse.

Clause 2: The system of clause 1, wherein the processing circuitry is further configured to output an indication of the propagation characteristic.

Clause 3: The system of any of clauses 1-2, wherein the propagation characteristic comprises one or more of: a first conduction velocity of the tissue for a first ECAP signal of the composite ECAP signal that is elicited by the first phase; a second conduction velocity of the tissue for a second ECAP signal of the s composite ECAP signal that is elicited by the second phase; a time delay between the first ECAP signal and the second ECAP signal; a first launch time between a calculated propagation time the first ECAP signal and a measured propagation time for the first ECAP signal; or a second launch time between a calculated propagation time the second ECAP signal and a measured propagation time for the second ECAP signal.

Clause 4: The system of clause 3, wherein the processing circuitry is configured to determine the first conduction velocity of the tissue based on a time delay between when the stimulation generation circuitry delivers the multiphasic stimulation pulse to the tissue of the patient and when the sensing circuitry senses the composite ECAP signal that is elicited by the multiphasic stimulation pulse.

Clause 5: The system of clause 4, wherein the processing circuitry is configured to determine the first launch time based on the first conduction of velocity of the tissue.

Clause 6: The system of any of clauses 1-5, wherein, to determine the propagation characteristic, the processing circuitry is configured to determine a time delay based on one or more of: a pulse width of one or more of the first phase or the second phase; an interval between the first phase and the second phase; or a spatial delay due to a spatial separation between a plurality of electrodes delivering the multiphasic stimulation pulse to the tissue.

Clause 7: The system of clause 6, wherein the processing circuitry is configured to determine the spatial delay based on a conduction velocity of the tissue.

Clause 8: The system of clause 7, wherein the processing circuitry is configured to: determine the conduction velocity of the tissue based on a time delay between when the stimulation generation circuitry delivers a reference multiphasic stimulation pulse to the tissue of the patient and when the sensing circuitry senses a reference composite ECAP signal elicited by the reference multiphasic stimulation pulse; and determine the spatial delay using the spatial separation and the conduction velocity.

Clause 9: The system of any of clauses 6-8, wherein the processing circuitry is configured to determine the time delay based on a summation of the pulse width, the interval, and the spatial delay.

Clause 10: The system of any of clauses 1-9, wherein the processing circuitry is further configured to control, based on the propagation characteristic, the stimulation generation circuitry to deliver the therapy to the patient.

Clause 11: The system of clause 10, wherein, to deliver the therapy, the processing circuitry is further configured to apply destructive interference between ECAP signals of the composite ECAP signal resulting from respective phases of the multiphasic stimulation pulse to reduce an amplitude of the composite ECAP signal that is elicited by the multiphasic stimulation pulse.

Clause 12: The system of clause 11, wherein, to apply destructive interference, the processing circuitry is configured to determine a pulse width of one or more of the first phase or the second phase that minimizes the amplitude of the composite ECAP signal that is elicited by the multiphasic stimulation pulse.

Clause 13: The system of any of clauses 11-12, wherein, to apply destructive interference, the processing circuitry is configured to determine a set of electrodes to deliver the therapy with a spatial separation that minimizes the amplitude of the composite ECAP signal that is elicited by the multiphasic stimulation pulse.

Clause 14: The system of any of clauses 11-13, wherein, to apply destructive interference, the processing circuitry is configured to determine an interval between the first phase and the second phase that minimizes the amplitude of composite ECAP signal that is elicited by the multiphasic stimulation pulse.

Clause 15: The system of clause 10, wherein, to deliver the therapy, the processing circuitry is further configured to apply constructive interference between ECAP signals of the composite ECAP signal resulting from respective phases of the multiphasic stimulation pulse to increase an amplitude of the composite ECAP signal that is elicited by the multiphasic stimulation pulse.

Clause 16: The system of clause 15, wherein, to apply constructive interference, the processing circuitry is configured to determine a pulse width of one or more of the first phase or the second phase that maximizes the amplitude of the composite ECAP signal that is elicited by the multiphasic stimulation pulse.

Clause 17: The system of any of clauses 15-16, wherein, to apply constructive destructive interference, the processing circuitry is configured to determine a set of electrodes to deliver the therapy with a spatial separation that maximizes the amplitude of the composite ECAP signal that is elicited by the multiphasic stimulation pulse.

Clause 18: The system of any of clauses 15-17, wherein, to apply constructive interference, the processing circuitry is configured to determine an interval between the first phase and the second phase that maximizes the amplitude of the composite ECAP signal that is elicited by the multiphasic stimulation pulse.

Clause 19: The system of any of clauses 10-18, wherein, to deliver the therapy, the processing circuitry is configured to: determine a target delay between the first phase and the second phase; and control the stimulation generation circuitry to provide one or more multiphasic stimulation pulse to the tissue of the patient that comprises the first phase of the multiphasic stimulation and the second phase of the multiphasic stimulation with the target delay.

Clause 20: The system of any of clauses 1-19, wherein the tissue comprises a spinal cord.

Clause 21: The system of any of clauses 1-20, wherein the second phase comprises an active recharge phase that balances charge to the tissue from the first phase.

Clause 22: The system of any of clauses 1-20, wherein the second phase comprises a passive recharge signal.

Clause 23: The system of any of clauses 1-22, wherein the therapy comprises one or more of spinal cord stimulation (SCS), deep brain stimulation (DBS), peripheral nerve stimulation (PNS), peripheral nerve field stimulation (PNFS), cortical stimulation (CS), pelvic floor stimulation, or gastrointestinal stimulation.

Clause 24: The system of any of clauses 1-23, further comprising an implantable medical device comprising the stimulation generation circuitry, sensing circuitry, memory, and processing circuitry.

Clause 25: A method comprising performing the operation of any of clauses 1-24.

Clause 26: A method comprising: controlling, by processing circuitry, stimulation generation circuitry to deliver, to a patient, multiphasic stimulation pulse that comprises a first phase and a second phase; determine, by the processing circuitry and with sensing circuitry, a composite evoked compound action potential (ECAP) signal elicited by the multiphasic stimulation pulse; and determine, by the processing circuitry and based on the composite ECAP signal, a propagation characteristic for the composite ECAP signal that is elicited by the multiphasic stimulation pulse.

Clause 27: The method of clause 26, further comprising outputting an indication of the propagation characteristic.

Clause 28: The method of any of clauses 26-27, wherein the propagation characteristic comprises one or more of: a first conduction velocity of the tissue for a first ECAP signal of the composite ECAP signal that is elicited by the first phase; a second conduction velocity of the tissue for a second ECAP signal of the s composite ECAP signal that is elicited by the second phase; a time delay between the first ECAP signal and the second ECAP signal; a first launch time between a calculated propagation time the first ECAP signal and a measured propagation time for the first ECAP signal; or a second launch time between a calculated propagation time the second ECAP signal and a measured propagation time for the second ECAP signal.

Clause 29: The method of clause 28, further comprising determining the first conduction velocity of the tissue based on a time delay between when the stimulation generation circuitry delivers the multiphasic stimulation pulse to the tissue of the patient and when the sensing circuitry senses the composite ECAP signal that is elicited by the multiphasic stimulation pulse.

Clause 30: The method of clause 29, further comprising determining the first launch time based on the first conduction of velocity of the tissue.

Clause 31: The method of any of clauses 26-30, wherein determining the propagation characteristic comprises determining a time delay based on one or more of: a pulse width of one or more of the first phase or the second phase; an interval between the first phase and the second phase; or a spatial delay due to a spatial separation between a plurality of electrodes delivering the multiphasic stimulation pulse to the tissue.

Clause 32: The method of clause 31, further comprising determining the spatial delay based on a conduction velocity of the tissue.

Clause 33: The method of clause 32, further comprising determining the conduction velocity of the tissue based on a time delay between when the stimulation generation circuitry delivers a reference multiphasic stimulation pulse to the tissue of the patient and when the sensing circuitry senses a reference composite ECAP signal elicited by the reference multiphasic stimulation pulse; and determine the spatial delay using the spatial separation and the conduction velocity.

Clause 34: The method of any of clauses 31-33, further comprising determining the time delay based on a summation of the pulse width, the interval, and the spatial delay.

Clause 35: The method of any of clauses 26-34, further comprising controlling, based on the propagation characteristic, the stimulation generation circuitry to deliver the therapy to the patient.

Clause 36: The method of clause 35, wherein delivering the therapy comprises applying destructive interference between ECAP signals of the composite ECAP signal resulting from respective phases of the multiphasic stimulation pulse to reduce an amplitude of the composite ECAP signal that is elicited by the multiphasic stimulation pulse.

Clause 37: The method of clause 36, wherein applying destructive interference comprises determining a pulse width of one or more of the first phase or the second phase that minimizes the amplitude of the composite ECAP signal that is elicited by the multiphasic stimulation pulse.

Clause 38: The method of any of clauses 36-37, wherein applying destructive interference comprises determining a set of electrodes to deliver the therapy with a spatial separation that minimizes the amplitude of the composite ECAP signal that is elicited by the multiphasic stimulation pulse.

Clause 39: The method of any of clauses 36-38, wherein applying destructive interference comprises determining an interval between the first phase and the second phase that minimizes the amplitude of composite ECAP signal that is elicited by the multiphasic stimulation pulse.

Clause 40: The method of clause 35, wherein, to deliver the therapy, the processing circuitry is further configured to apply constructive interference between ECAP signals of the composite ECAP signal resulting from respective phases of the multiphasic stimulation pulse to increase an amplitude of the composite ECAP signal that is elicited by the multiphasic stimulation pulse.

Clause 41: The method of clause 40, wherein applying constructive interference comprises determining a pulse width of one or more of the first phase or the second phase that maximizes the amplitude of the composite ECAP signal that is elicited by the multiphasic stimulation pulse.

Clause 42: The method of any of clauses 40-41, wherein applying constructive destructive interference comprises determining a set of electrodes to deliver the therapy with a spatial separation that maximizes the amplitude of the composite ECAP signal that is elicited by the multiphasic stimulation pulse.

Clause 43: The method of any of clauses 40-42, wherein applying constructive interference comprises determining an interval between the first phase and the second phase that maximizes the amplitude of the composite ECAP signal that is elicited by the multiphasic stimulation pulse.

Clause 44: The method of any of clauses 35-43, wherein delivering the therapy comprises: determining a target delay between the first phase and the second phase; and controlling the stimulation generation circuitry to provide one or more multiphasic stimulation pulse to the tissue of the patient that comprises the first phase of the multiphasic stimulation and the second phase of the multiphasic stimulation with the target delay.

Clause 45: The method of any of clauses 26-43, wherein the tissue comprises a spinal cord.

Clause 46: The method of any of clauses 26-44, wherein the second phase comprises an active recharge phase that balances charge to the tissue from the first phase.

Clause 47: The method of any of clauses 26-44, wherein the second phase comprises a passive recharge signal.

Clause 48: The method of any of clauses 26-47, wherein the therapy comprises one or more of spinal cord stimulation (SCS), deep brain stimulation (DBS), peripheral nerve stimulation (PNS), peripheral nerve field stimulation (PNFS), cortical stimulation (CS), pelvic floor stimulation, or gastrointestinal stimulation.

Clause 49: The method of any of clauses 26-48, further comprising an implantable medical device comprising the stimulation generation circuitry, sensing circuitry, memory, and processing circuitry.

Clause 50: A medical device comprising: stimulation generation circuitry configured to deliver a multiphasic stimulation pulse to the patient; sensing circuitry configured to sense evoked compound action potential (ECAP) signals elicited by the multiphasic stimulation pulse; and processing circuitry electrically connected to the sensing circuitry and the stimulation generation circuitry, the processing circuitry being configured to: control the stimulation generation circuitry to deliver the multiphasic stimulation pulse that comprises a first phase and a second phase; and determine, based on the ECAP signals, a propagation characteristic for a set of the ECAP signals that are elicited by the multiphasic stimulation pulse.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), such as, for example, ferroelectric RAM (FRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
stimulation generation circuitry configured to deliver a multiphasic stimulation pulse to a patient;
sensing circuitry configured to sense a composite evoked compound action potential (ECAP) signal elicited by the multiphasic stimulation pulse; and
processing circuitry electrically connected to the sensing circuitry and the stimulation generation circuitry, the processing circuitry being configured to:
control the stimulation generation circuitry to deliver the multiphasic stimulation pulse that comprises a first phase and a second phase; and
determine, based on the composite ECAP signal, a propagation characteristic, wherein the composite ECAP signal comprises a summation of a first ECAP signal corresponding to the first phase of the multiphasic stimulation pulse and a second ECAP signal corresponding to the second phase of the multiphasic stimulation pulse, and wherein the propagation characteristic is associated with interference between the first ECAP signal and the second ECAP signal of the composite ECAP signal that is elicited by the multiphasic stimulation pulse.

2. The system of claim 1, wherein the processing circuitry is further configured to output an indication of the propagation characteristic.

3. The system of claim 1, wherein the propagation characteristic comprises one or more of:
a first conduction velocity of tissue of the patient for a first ECAP signal of the composite ECAP signal that is elicited by the first phase;
a second conduction velocity of the tissue for a second ECAP signal of the composite ECAP signal that is elicited by the second phase;
a time delay between the first ECAP signal and the second ECAP signal;
a first launch time between a calculated propagation time the first ECAP signal and a measured propagation time for the first ECAP signal; or
a second launch time between a calculated propagation time the second ECAP signal and a measured propagation time for the second ECAP signal.

4. The system of claim 3, wherein the processing circuitry is configured to determine the first conduction velocity of the tissue based on a time delay between when the stimulation generation circuitry delivers the multiphasic stimulation pulse to the tissue of the patient and when the sensing circuitry senses the composite ECAP signal that is elicited by the multiphasic stimulation pulse.

5. The system of claim 4, wherein the processing circuitry is configured to determine the first launch time based on the first conduction of velocity of the tissue.

6. The system of claim 1, wherein, to determine the propagation characteristic, the processing circuitry is configured to determine a time delay based on one or more of:
a pulse width of one or more of the first phase or the second phase;
an interval between the first phase and the second phase; or
a spatial delay due to a spatial separation between a plurality of electrodes delivering the multiphasic stimulation pulse to tissue of the patient.

7. The system of claim 6, wherein the processing circuitry is configured to determine the spatial delay based on a conduction velocity of the tissue.

8. The system of claim 7, wherein the processing circuitry is configured to:
determine the conduction velocity of the tissue based on a time delay between when the stimulation generation circuitry delivers a reference multiphasic stimulation pulse to the tissue of the patient and when the sensing circuitry senses a reference composite ECAP signal elicited by the reference multiphasic stimulation pulse; and
determine the spatial delay using the spatial separation and the conduction velocity.

9. The system of claim 6, wherein the processing circuitry is configured to determine the time delay based on a summation of the pulse width, the interval, and the spatial delay.

10. The system of claim 1, wherein the processing circuitry is further configured to control, based on the propagation characteristic, the stimulation generation circuitry to deliver therapy to the patient.

11. The system of claim 10, wherein, to deliver the therapy, the processing circuitry is further configured to apply destructive interference between ECAP signals of the composite ECAP signal resulting from respective phases of the multiphasic stimulation pulse to reduce an amplitude of the composite ECAP signal that is elicited by the multiphasic stimulation pulse.

12. The system of claim 11, wherein, to apply destructive interference, the processing circuitry is configured to determine a pulse width of one or more of the first phase or the second phase that minimizes the amplitude of the composite ECAP signal that is elicited by the multiphasic stimulation pulse.

13. The system of claim 11, wherein, to apply destructive interference, the processing circuitry is configured to determine a set of electrodes to deliver the therapy with a spatial separation that minimizes the amplitude of the composite ECAP signal that is elicited by the multiphasic stimulation pulse.

14. The system of claim 11, wherein, to apply destructive interference, the processing circuitry is configured to determine an interval between the first phase and the second phase that minimizes the amplitude of composite ECAP signal that is elicited by the multiphasic stimulation pulse.

15. The system of claim 10, wherein, to deliver the therapy, the processing circuitry is further configured to apply constructive interference between ECAP signals of the composite ECAP signal resulting from respective phases of the multiphasic stimulation pulse to increase an amplitude of the composite ECAP signal that is elicited by the multiphasic stimulation pulse.

16. The system of claim 15, wherein, to apply constructive interference, the processing circuitry is configured to determine a pulse width of one or more of the first phase or the second phase that maximizes the amplitude of the composite ECAP signal that is elicited by the multiphasic stimulation pulse.

17. The system of claim 15, wherein, to apply constructive destructive interference, the processing circuitry is configured to determine a set of electrodes to deliver the therapy with a spatial separation that maximizes the amplitude of the composite ECAP signal that is elicited by the multiphasic stimulation pulse.

18. The system of claim 15, wherein, to apply constructive interference, the processing circuitry is configured to determine an interval between the first phase and the second phase that maximizes the amplitude of the composite ECAP signal that is elicited by the multiphasic stimulation pulse.

19. The system of claim 10, wherein, to deliver the therapy, the processing circuitry is configured to:
determine a target delay between the first phase and the second phase; and
control the stimulation generation circuitry to provide one or more multiphasic stimulation pulse to tissue of the patient that comprises the first phase of the multiphasic stimulation and the second phase of the multiphasic stimulation with the target delay.

20. The system of claim 3, wherein the tissue comprises a spinal cord.

21. The system of claim 1, wherein the second phase comprises an active recharge phase that balances charge to tissue of the patient from the first phase.

22. The system of claim 1, wherein the second phase comprises a passive recharge signal.

23. A method comprising:

controlling, by processing circuitry, stimulation generation circuitry to deliver, to a patient, multiphasic stimulation pulse that comprises a first phase and a second phase;

determine, by the processing circuitry and with sensing circuitry, a composite evoked compound action potential (ECAP) signal elicited by the multiphasic stimulation pulse, wherein the composite ECAP signal comprises a summation of a first ECAP signal corresponding to the first phase of the multiphasic stimulation pulse and a second ECAP signal corresponding to the second phase of the multiphasic stimulation pulse; and determine, by the processing circuitry and based on the composite ECAP signal, a propagation characteristic associated with interference between the first ECAP signal and the second ECAP signal of the composite ECAP signal that is elicited by the multiphasic stimulation pulse.

24. The method of claim 23, further comprising outputting, by the processing circuitry, an indication of the propagation characteristic.

25. The method of claim 23, wherein the propagation characteristic comprises one or more of:

a first conduction velocity of tissue of the patient for a first ECAP signal of the composite ECAP signal that is elicited by the first phase;

a second conduction velocity of the tissue for a second ECAP signal of the composite ECAP signal that is elicited by the second phase;

a time delay between the first ECAP signal and the second ECAP signal;

a first launch time between a calculated propagation time the first ECAP signal and a measured propagation time for the first ECAP signal; or a second launch time between a calculated propagation time the second ECAP signal and a measured propagation time for the second ECAP signal.

26. The method of claim 25, further comprising determining, by the processing circuitry, the first conduction velocity of the tissue based on a time delay between when the stimulation generation circuitry delivers the multiphasic stimulation pulse to the tissue of the patient and when the sensing circuitry senses the composite ECAP signal that is elicited by the multiphasic stimulation pulse.

27. The method of claim 26, further comprising determining the first launch time based on the first conduction of velocity of the tissue.

28. The method of claim 23, wherein determining the propagation characteristic comprises determining a time delay based on one or more of:

a pulse width of one or more of the first phase or the second phase;

an interval between the first phase and the second phase; or a spatial delay due to a spatial separation between a plurality of electrodes delivering the multiphasic stimulation pulse to tissue of the patient.

29. A medical device comprising:

stimulation generation circuitry configured to deliver a multiphasic stimulation pulse to a patient;

sensing circuitry configured to sense a composite evoked compound action potential (ECAP) signal elicited by the multiphasic stimulation pulse; and processing circuitry electrically connected to the sensing circuitry and the stimulation generation circuitry, the processing circuitry being configured to:

control the stimulation generation circuitry to deliver the multiphasic stimulation pulse that comprises a first phase and a second phase; and determine, based on the composite ECAP signal, a propagation characteristic, wherein the composite ECAP signal comprises a summation of a first ECAP signal corresponding to the first phase of the multiphasic stimulation pulse and a second ECAP signal corresponding to the second phase of the multiphasic stimulation pulse, and wherein the propagation characteristic is associated with interference between the first ECAP signal and the second ECAP signal of the composite ECAP signal that is elicited by the multiphasic stimulation pulse.

* * * * *